(12) United States Patent
Gopal

(10) Patent No.: US 9,464,066 B2
(45) Date of Patent: Oct. 11, 2016

(54) DEUTERATED COMPOUNDS USEFUL FOR TREATING NEURODEGENERATIVE DISEASES

(71) Applicant: PharmatrophiX, Inc., Menlo Park, CA (US)

(72) Inventor: Damodara Gopal, Concord, OH (US)

(73) Assignee: Pharmatrophix, Inc., Menlo Park, CA (US)

( * ) Notice: Subject to any disclaimer, the term of this patent is extended or adjusted under 35 U.S.C. 154(b) by 0 days.

(21) Appl. No.: 14/230,833

(22) Filed: Mar. 31, 2014

(65) Prior Publication Data

US 2016/0229823 A1 Aug. 11, 2016

Related U.S. Application Data

(63) Continuation of application No. 13/512,839, filed as application No. PCT/US2010/058345 on Nov. 30, 2010, now abandoned.

(60) Provisional application No. 61/264,933, filed on Nov. 30, 2009.

(51) Int. Cl.

| A61K 31/535 | (2006.01) |
|---|---|
| C07D 295/135 | (2006.01) |
| C07D 241/08 | (2006.01) |
| C07D 233/72 | (2006.01) |
| C07K 5/062 | (2006.01) |
| C07D 295/13 | (2006.01) |
| C07D 473/08 | (2006.01) |
| C07D 233/61 | (2006.01) |
| A61K 38/00 | (2006.01) |

(52) U.S. Cl.
CPC ......... *C07D 295/135* (2013.01); *C07D 233/61* (2013.01); *C07D 233/72* (2013.01); *C07D 241/08* (2013.01); *C07D 295/13* (2013.01); *C07D 473/08* (2013.01); *C07K 5/06034* (2013.01); *A61K 38/00* (2013.01)

(58) Field of Classification Search
CPC ............... A61K 38/00; A61K 31/437; A61K 31/4166; A61K 31/5377
See application file for complete search history.

(56) References Cited

U.S. PATENT DOCUMENTS 6,029,114 A 2/2000 Shamovsky et al.
2002/0028827 A1* 3/2002 Naicker ................ A61L 31/16
514/291

FOREIGN PATENT DOCUMENTS

WO  WO 2005/051919 A1  6/2005
WO  WO 2006/113097 A2  10/2006

OTHER PUBLICATIONS

Chapter 13: Spectroscopy, Organic Chemistry 4e Carey, 2000, The McGraw-Hill Companies available on-line at: http://www. m h he.com/physsci/chem istry/carey/student/olc/ch 13n mr. html., 17 pages.
Culp et al., J. Agrlc. Food Chem. 1992, 40, 1892-1897.
International Preliminary Report on Patentability for International Application No. PCT/US201 0/058345, mailed on May 4, 2011.
International Search Report for International Application No. PCT/US2010/058345, mailed on May 11, 2011.
Written Opinion for International Application No. PCT/US201 0/058345, mailed on May 11, 2011.

* cited by examiner

*Primary Examiner* — James H Alstrum Acevedo
*Assistant Examiner* — Kaipeen Yang
(74) *Attorney, Agent, or Firm* — Wilson Sonsini Goodrich & Rosati

(57) ABSTRACT

The present application is related to deuterated compounds which are novel neurotrophin mimetics. The application also discloses the treatment of disorders involving degradation or dysfunction of cells expressing p75 in a mammal by administering an effective amount of such deuterated compounds.

13 Claims, 1 Drawing Sheet

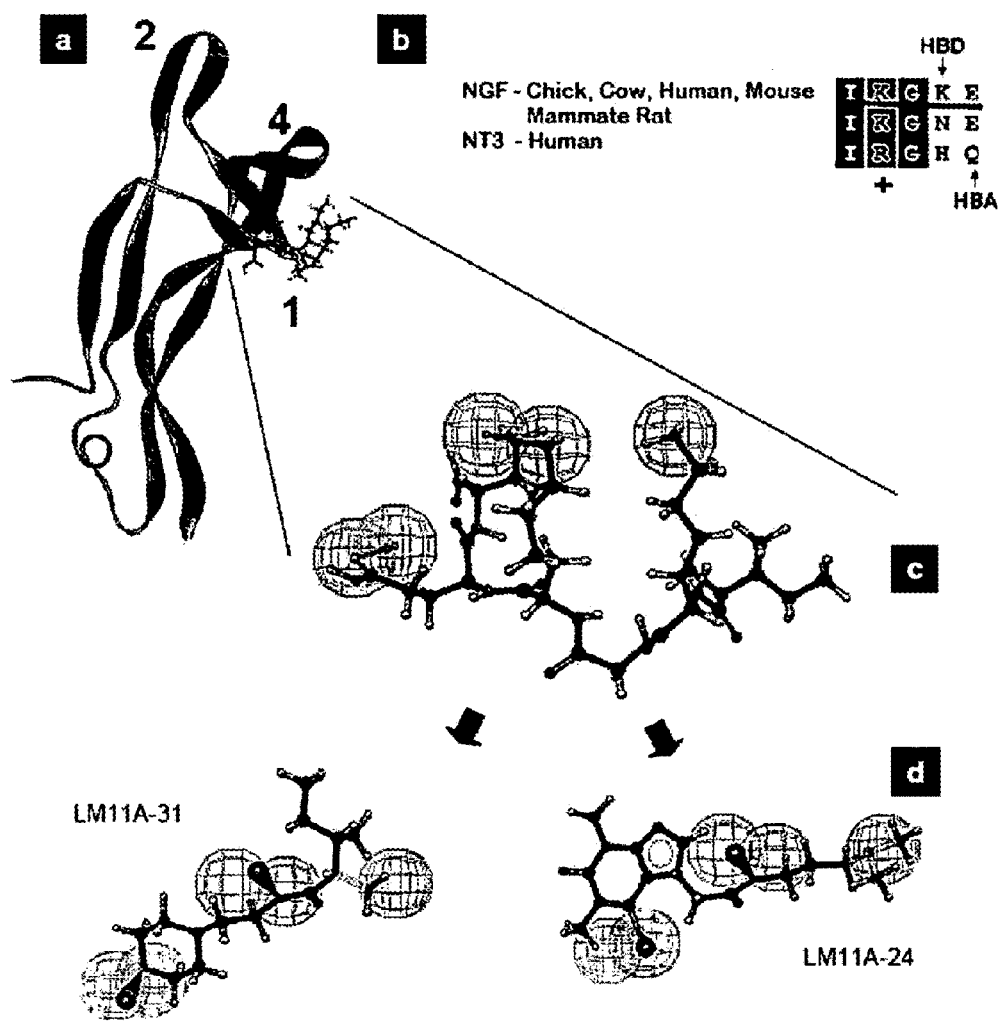

DEUTERATED COMPOUNDS USEFUL FOR TREATING NEURODEGENERATIVE DISEASES

CROSS-REFERENCE TO RELATED APPLICATION

The present application is a continuation of U.S. patent application Ser. No. 13/512,839, a U.S. national stage application under 35 U.S.C. §371 of International Application No. PCT/US2010/058345, filed on Nov. 30, 2010, which claims the benefit of U.S. Provisional Application No. 61/264,933, filed on Nov. 30, 2009 and entitled "DEUTERATED COMPOUNDS USEFUL FOR TREATING NEURODEGENERATIVE DISEASES". The present application claims priority to the above-referenced applications, the contents of each of which are hereby incorporated by reference in their entireties for all purposes.

TECHNICAL FIELD

The present application generally relates to the treatment of disorders involving degradation or dysfunction of cells expressing p75, including, for example neurodegenerative disorders. More particularly, the methods of the present application relate to administering to a subject an effective amount of a deuterated compound having binding specificity for a $p75^{NTR}$ molecule to treat a disorder involving degradation or dysfunction of cells expressing p75.

BACKGROUND

Neurotrophins are polypeptides that play a role in the development, function, and/or survival of certain cells, including neurons, oligodendrocytes, Schwann cells, hair follicle cells, and other cells. The death or dysfunction of neurons and other cell types has been directly implicated in a number of neurodegenerative disorders. It has been suggested that alterations in neurotrophin localization, expression levels of neurotrophins, and/or expression levels of the receptors that bind neurotrophins are therefore linked to neuronal degeneration. Degeneration occurs in the neurodegenerative disorders Alzheimer's, Parkinson's and ALS, among others. Degeneration of oligodendrocytes can occur in central nervous system injury, multiple sclerosis, and other pathological states.

A variety of neurotrophins have been identified, including Nerve Growth Factor (NGF), Neurotrophin-3 (NT-3), Neurotrophin-4/5 (NT-4/5), Neurotrophin 6 (NT-6) and Brain Derived Neurotrophic Factor (BDNF). Neurotrophins are found in both precursor form, known as pro-neurotrophins, and in mature form. The mature forms are proteins of about 120 amino acids in length that exist in physiological states as stable, non-covalent approximately 25 kDa homodimers. Each neurotrophin monomer includes three solvent-exposed β-hairpin loops, referred to as loops 1, 2, and 4 that exhibit relatively high degrees of amino acid conservation across the neurotrophin family.

Mature neurotrophins bind preferentially to the receptors Trk and $p75^{NTR}$ (p75 neurotrophin receptor, also called the Low Affinity Nerve Growth Factor Receptor or LNGFR) while pro-neurotrophins, which contain an N-terminal domain proteolytically removed in mature forms, interact principally with $p75^{NTR}$ and through their N-terminal domains, with the sorting receptor sortilin (Fahnestock, M., et al. (2001) Mol Cell Neurosci 18, 210-220; Harrington, A. W. et al. (2004) Proc Natl Acad Sci USA 101, 6226-6230; Nykjaer. A. et al., (2004) Nature 427, 843-848). $p75^{NTR}$ interacts with Trks and modulates Trk signaling, but is also independently coupled to several signaling systems, including pro-survival signals, IRAK/TRAF6/NF.kappa.B, PI3/AKT, and pro-apoptotic signals, NRAGE/JNK (Mamidipudi, V., et al. (2002) J Biol Chem 277, 28010-28018; Roux, P. P., et al. (2001) J Biol Chem 276, 23097-23104; Salehi, A. H., et al. (2000) Neuron 27, 279-288).

Biological molecules and small molecules binding to $p75^{NTR}$ can be useful therapeutic entities for treating various disease conditions associated with $p75^{NTR}$. With respect to small molecules, deuterium-substitution is one of many approaches to provide variations of compounds potentially useful for therapeutic treatment. General exposure to and incorporation of deuterium is safe within levels potentially achieved by use of compounds of this invention as medicaments. For instance, the weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects. Although higher deuterium concentrations, usually in excess of 20%, may be toxic in animals, acute replacement of as high as 15% to 23% of the hydrogen in humans' fluids with deuterium has been found to not cause toxicity. In a 70 kg human male, 15% replacement of the hydrogen in the fluid compartment with deuterium corresponds to incorporation of approximately 1 kg of deuterium or the equivalent of approximately 5 kg of deuterated water. Deuterium tracers, such as deuterium-labeled drugs and doses, in some cases repeatedly, of thousands of milligrams of deuterated water, are also used in healthy humans of all ages, including neonates and pregnant women, without reported incident.

There is a need in the art for the development of small molecule agents with favorable drug-like features based upon neurotrophins that are capable of targeting specific neurotrophin receptors for use in the treatment of disorders or diseases.

SUMMARY

Briefly, this application generally discloses deuterated compounds having binding specificity for $p75^{NTR}$, as well as to methods for the preparation and use of such compounds, and to pharmaceutical compositions containing the same. More specifically, deuterated compounds of the present application are represented by the general structures:

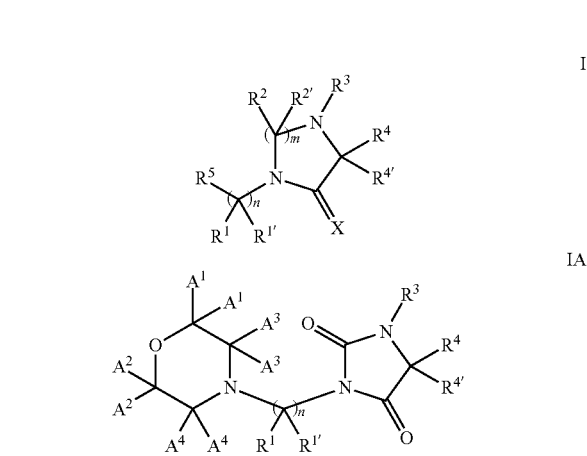

-continued

IB
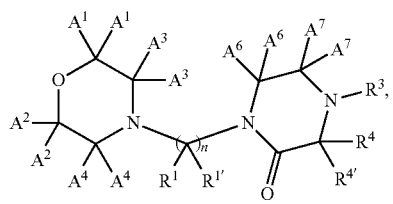

II
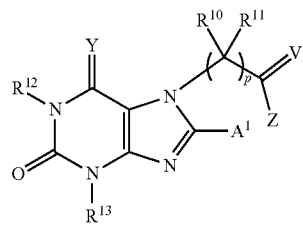

IIA
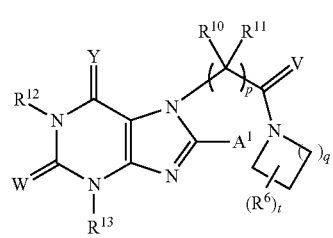

IIB
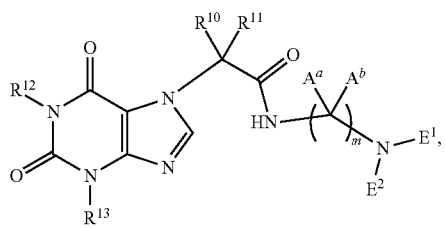

IIIA
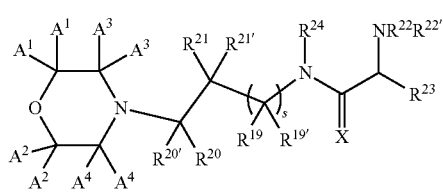

IIIB
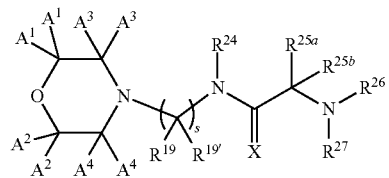

IV
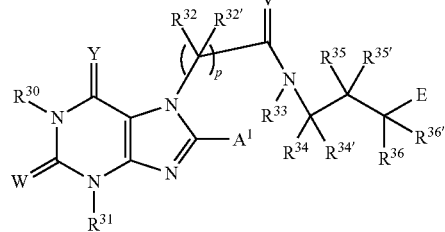

including pharmaceutically acceptable salts, esters, solvates, and prodrugs thereof, wherein $R^1$, $R^{1'}$, $R^2$, $R^{2'}$, $R^3$, $R^4$, $R^{4'}$, $R^5$, $R^6$, $R^{10}$, $R^{11}$, $R^{12}$, $R^{13}$, $R^{19}$, $R^{19'}$, $R^{20}$, $R^{20'}$, $R^{21}$, $R^{21'}$, $R^{22}$, $R^{23}$, $R^{24}$, $R^{30}$, $R^{31}$, $R^{32}$, $R^{32'}$, $R^{33}$, $R^{34}$, $R^{34'}$, $R^{35}$, $R^{35'}$, $R^{36}$, $R^{36'}$, $A^1$, $A^2$, $A^3$, $A^4$, E, $E^1$, $E^2$, V, W, X, Y, Z m, n, p, q, r, s, t, are as defined below.

BRIEF DESCRIPTION OF THE DRAWINGS

FIG. 1a is a ribbon representation of the X-ray crystal structure of human NGF with β-turn loops 1, 2, and 4 designated. The average side chain positions for loop 1 are illustrated.

FIG. 1b represents the comparison of peptide sequences (SEQ ID NOs:1-3) of loop 1 from NGF and NT3 from the indicated species and the assignment of pharmacophores. Positively ionizable groups are signified by "+". "HBD" and "HBA" represent hydrogen bond donor and hydrogen bond acceptor, respectively.

FIG. 1c shows application of the pharmacophoric features to a 3D loop model. Hydrogen bonding features are represented by pairs of spheres with their relative positions indicating the locations of the acceptor and the donor. One of the spheres of the pair is centered on putative acceptor/donor features in the model, while the other indicates the target location of a complementary feature on any potentially interacting molecule. The diameter of the spheres represents the spatial tolerance for chemical feature matching in 3D conformer library scans.

FIG. 1d is a 3D loop model disclosing representative fits to the pharmacophore of the protonated analogs of two compounds found to be active as disclosed herein.

DETAILED DESCRIPTION

In subjects with disorders related to degeneration or dysfunction of cells expressing p75, such as neurodegenerative disorders, alterations in neurotrophin localization, expression levels of neurotrophins, expression levels of the receptors that bind neurotrophins, and/or receptor signaling and functional outcomes can occur. Accordingly, by providing subjects suffering from such disorders with a corresponding neurotrophic factor or mimetic thereof that modulates $p75^{NTR}$ function or proNGF/NGF binding to prevent cellular degeneration or dysfunction, such neural degeneration can be alleviated or prevented. As disclosed herein, methods of treating neurodegenerative and other disorders and/or facilitating cell survival by administering a deuterated compound having binding specificity for a $p75^{NTR}$ molecule are provided.

The methods and compounds of the present application relate to deuterated compounds having binding specificity for a $p75^{NTR}$ molecule. Deuterated compounds having binding specificity for $p75^{NTR}$ are suitable for positively regulating survival of neural and other cells, analogous to the determination that the protonated analogs that have binding specificity for $p75^{NTR}$ are suitable for regulating survival of neural and other cells. Particularly, in cells showing trophic responses to neurotrophins or cells expressing $p75^{NTR}$ either constitutively or in response to injury or disease, the deuterated compounds disclosed in the present application promote survival signaling. In cells susceptible to neurotrophin-induced death, the deuterated compounds do not induce apoptosis, but inhibit neurotrophin-mediated death.

General exposure to and incorporation of deuterium is safe within levels potentially achieved by use of compounds of this invention as medicaments. For instance, the weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects. Although higher deuterium concentrations, usually in excess of 20%, may be toxic in animals, acute replacement of as high as 15% to 23% of the hydrogen in humans' fluids with deuterium has been found to not cause toxicity. In a 70 kg human male, 15% replacement of the hydrogen in the fluid compartment with deuterium corresponds to incorporation of approximately 1 kg of deuterium or the equivalent of approximately 5 kg of deuterated water. Deuterium tracers, such as deuterium-labeled drugs and doses, in some cases repeatedly, of thousands of milligrams of deuterated water, are also used in healthy humans of all ages, including neonates and pregnant women, without reported incident. Thus, it is clear that any deuterium released, for instance, during the metabolism of compounds of this invention poses no health risk.

Additional embodiments and advantages of the application will be set forth in part in the description that follows, and in part will be obvious from the description, or may be learned by practice of the invention. It is to be understood that both the foregoing general description and the following detailed description are exemplary and explanatory only and are not restrictive of the invention as claimed.

DEFINITIONS

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±20% or ±10%, in another example ±5%, in another example ±1%, and in yet another example ±0.1% from the specified amount, as such variations are appropriate to perform the disclosed method.

As used herein, the phrase "a disorder involving degeneration or dysfunction of cells expressing p75" includes, but is not limited to disorders related to upregulation of p75. Such disorders include neurodegenerative disorders, as well as conditions involving degeneration of $p75^{NTR}$-expressing cells, such as hair loss. Within the nervous system, the p75 receptor is expressed by various cell types including neurons, oligodendrocytes, astrocytes. Compounds targeting p75 receptors expressed by neurons can be used to prevent loss of function, degeneration and/or death of neurons in a number of nervous system disorders including (but not limited to) Alzheimer's disease, Parkinson's disease, Huntington's disease, stroke, traumatic brain injury, spinal cord injury, epilepsy, multiple sclerosis, amyotrophic lateral sclerosis, neuropathies, myopathies and various forms of retinal degeneration. In each of these disorders, neurons expressing p75 are affected.

Deuterated compounds targeting p75 receptors expressed by oligodendrocytes can be used to prevent loss of function, degeneration and/or death of oligodendrocytes in a number of nervous system disorders including (and not limited to) multiple sclerosis, spinal cord injury and perinatal anoxia.

Outside of the nervous system, a number of cell populations express the p75 receptor. These include hair follicle cells, hepatic cells, vascular endothelial, vascular smooth muscle cells, cardiomyocytes. In addition, the p75 receptor is expressed by certain tumor cells such as those involved in breast or prostate cancer. Given this expression pattern, deuterated compounds targeting p75 receptors can be used for the following indications: to prevent loss of hair follicle cells and thereby prevent hair loss; to prevent hepatic cirrhosis and promote liver regeneration; to regulate angiogenesis and promote neovascularization in the setting of diabetic wounds or other ischemic settings; to prevent cardiomyopathy by preventing myocardial cell loss or by stimulating growth of new cardiomyocytes either in the setting of ischemia or after myocardial infarction; and to inhibit tumor cell growth. In addition p75 is expressed by stem cells and is known to regulate stem cell growth; therefore, p75 ligands can be used to promote stem cell growth as part of a strategy to promote tissue and organ regeneration.

As used herein, the term "neurodegenerative disorder" includes any disorder characterized by neural damage and includes but is not limited to Alzheimer's disease, Huntington's disease, Pick's disease, amyotrophic lateral sclerosis, epilepsy, Parkinson's disease, spinal cord injury, stroke, hypoxia, ischemia, brain injury, diabetic neuropathy, peripheral neuropathy, nerve transplantation, multiple sclerosis, and peripheral nerve injury. The deuterated compounds disclosed herein function as ligands at the p75 neurotrophin receptor and thereby induce intracellular signaling that prevents cellular degeneration or death and/or upregulates cell function or growth. The intracellular signaling mechanisms regulated by the p75 receptor are fundamental mechanisms present in essentially all cell types; therefore, it is expected that any cell or tissue expressing this receptor would be amendable to treatment with these deuterated compounds for the goal of preventing cellular or tissue degeneration, promoting cell survival and/or for upregulating function or growth.

The term "alkyl," alone or in combination, refers to an optionally substituted straight-chain or branched-chain alkyl radical having from 1 to about 20 carbon atoms. The term also includes optionally substituted straight-chain or branched-chain alkyl radicals having from 1 to about 6 carbon atoms as well as those having from 1 to about 4 carbon atoms. Examples of alkyl radicals include methyl, ethyl, n-propyl, isopropyl, n-butyl, isobutyl, sec-butyl, tert-butyl, tert-amyl, pentyl, hexyl, heptyl, octyl and the like. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls. Alkyl groups can be optionally substituted.

The term "heteroalkyl" refers to alkyl groups, as described above, in which one or more skeletal atoms are oxygen, nitrogen, sulfur or combinations thereof. The term heteroalkyl also includes alkyl groups in which one 1 to about 6 skeletal atoms are oxygen, nitrogen, sulfur or combinations thereof, as well as those in which 1 to 4 skeletal atoms are oxygen, nitrogen, sulfur or combinations thereof and those in which 1 to 2 skeletal atoms are oxygen, nitrogen, sulfur or combinations thereof. Heteroalkyl groups are optionally substituted.

The term "alkenyl," alone or in combination, refers to an optionally substituted straight-chain or branched-chain hydrocarbon radical having one or more carbon-carbon double-bonds and having from 2 to about 18 carbon atoms. The term also includes optionally substituted straight-chain or branched-chain hydrocarbon radicals having one or more carbon-carbon double bonds and having from 2 to about 6 carbon atoms as well as those having from 2 to about 4 carbon atoms. Examples of alkenyl radicals include ethenyl, propenyl, butenyl, 1,4-butadienyl and the like. Suitable alkenyl groups include allyl. The terms "allylic group" or "allyl" refer to the group —CH$_2$HC=CH$_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic." "1-alkenyl" refers to alkenyl groups where the double bond is between the first and second carbon atom.

The term "alkynyl," alone or in combination, refers to an optionally substituted straight-chain or branched-chain hydrocarbon radical having one or more carbon-carbon triple-bonds and having from 2 to about 12 carbon atoms. The term also includes optionally substituted straight-chain or branched-chain hydrocarbon radicals having one or more carbon-carbon triple bonds and having from 2 to about 6 carbon atoms as well as those having from 2 to about 4 carbon atoms. Examples of alkynyl radicals include ethynyl, propynyl, butynyl and the like. "1-alkynyl" refers to alkynyl groups where the triple bond is between the first and second carbon atom.

"Cyclic alkyl" and "cycloalkyl" refer to a non-aromatic mono- or multicyclic ring system of about 3 to about 10 carbon atoms, e.g., 3, 4, 5, 6, 7, 8, 9, or 10 carbon atoms, alternately from about 3 to about 6 carbon atoms. The cycloalkyl group can be optionally partially unsaturated. The cycloalkyl group also can be optionally substituted as defined herein. Representative monocyclic cycloalkyl rings include, but are not limited to, cyclopropyl, cyclobutyl, cyclopentyl, cyclohexyl, cycloheptyl, and the like. Further, the cycloalkyl group can be optionally substituted with a linking group, such as an alkylene group as defined hereinabove, for example, methylene, ethylene, propylene, and the like. In such cases, the cycloalkyl group can be referred to as, for example, cyclopropylmethyl, cyclobutylmethyl, and the like. Additionally, multicyclic cycloalkyl rings include adamantyl, octahydronaphthyl, decalin, camphor, camphane, and noradamantyl.

The term "heterocyclic alkyl" and "heterocycloalkyl" refer to cyclic groups of 3 to 6 atoms, or 3 to 10 atoms, containing at least one heteroatom. In one aspect, these groups contain 1 to 3 heteroatoms. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, morpholinoethyl, and pyridyl. Such groups may be substituted.

The term "aryl" refers to aromatic groups which have 5-14 ring atoms and at least one ring having a conjugated pi electron system and includes carbocyclic aryl, heterocyclic aryl and biaryl groups, all of which may be optionally substituted. The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The aromatic ring(s) can comprise phenyl, naphthyl, biphenyl, diphenylether, diphenylamine and benzophenone, among others. all of which can be optionally substituted. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings. Examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like, all optionally substituted.

"Carbocyclic aryl" groups are groups wherein the ring atoms on the aromatic ring are carbon atoms. Carbocyclic aryl groups include monocyclic carbocyclic aryl groups and polycyclic or fused compounds such as optionally substituted naphthyl groups.

"Heterocyclic aryl" or "heteroaryl" groups are groups having from 1 to 4 heteroatoms as ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The phrase "carbocyclic ring" refers to a saturated or unsaturated monocyclic or bicyclic ring in which all atoms of all rings are carbon. Thus, the term includes cycloalkyl and carbocyclic aryl rings.

The phrase "heterocyclic ring" refers to a saturated or unsaturated monocyclic or bicyclic ring having from 1 to 4 heteroatoms as ring atoms in the aromatic ring and the remainder of the ring atoms being carbon atoms. Thus, the term includes heterocycloalkyl and heterocyclic aryl rings.

The term "optionally substituted" or "substituted" includes groups substituted by one to four substituents, independently selected from lower alkyl, lower aryl, lower aralkyl, lower alicyclic, heterocyclic alkyl, hydroxyl, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl.

When a named atom of a ring or chain is defined as being "absent," the named atom is replaced by a direct bond or is incorporated into double bond along with the atom to which it is attached. When the linking group or spacer group is defined as being absent, the linking group or spacer group is replaced by a direct bond.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Alkoxyl" or "alkoxyalkyl" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —$NH_2$ group.

The term "carbonyl" refers to the —(C=O)— group.

The term "carboxyl" refers to the —COOH group.

The term "cyano" refers to the —CN group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to =O.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term "cycloalkenyl" refers to a partially unsaturated cyclic hydrocarbon group containing one or more rings, for example, one ring, two rings, three rings, or four rings, with three or more carbon atoms per ring, for example, 3, 4, 5, 6, 7, or 8 carbon atoms per ring. Exemplary cycloalkenyl groups include, but are not limited to, cyclopropenyl, cyclobutenyl, cyclopentenyl, cyclohexenyl, and the like. Cycloalkenyl groups can be optionally substituted, such as with one or more substituents, e.g. 1, 2, 3, or 4 substituents, at any available point of attachment. Exemplary substituents include, but are not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

The term "deuterium" refers to an isotope of hydrogen that has one proton and one neutron in its nucleus and that has twice the mass of ordinary hydrogen. Deuterium can be represented by symbols such as "$^2H$" or "D". The term "deuterated" herein, by itself or used to modify a compound or group, refers to replacement of one or more hydrogen atom(s), which is attached to carbon(s), with a deuterium atom. For example, the term "deuterated compound" refers to a compound wherein one or more carbon-bound hydrogen(s) are replaced by one or more deuterium(s). Similarly, the term "deuterated" is be used herein to modify a chemical structure in phrases like "a deuterated form of the following structure" or "the following structure(s) in a deuterated form"; a chemical name, such as "deuterated-(2S,3S)-2-amino-3-methyl-N-(2-morpholinoethyl)-pentanamide"; or an organic group or radical, such as "deuterated-alkyl", "deuterated-cycloalkyl", "deuterated-heterocycloalkyl", "deuterated-aryl", "deuterated-morpholinyl", and the like.

The phrase "deuterated-alkyl" refers to an alkyl group as defined herein, wherein at least one hydrogen atom bound to carbon is replaced by a deuterium. That is, in a deuterated alkyl group, at least one carbon atom is bound to a deuterium. In a deuterated alkyl group, it is possible for a carbon atom to be bound to more than one deuterium; it is also possible that more than one carbon atom in the alkyl group is bound to a deuterium. Analogously, the term "deuterated" and the phrases "deuterated-heterocycloalkyl," deuterated-heteroaryl," "deuterated-cycloalkyl," "deuterated-heterocycloalkyl," "deuterated-aryl," "deuteratedy-acyl," "deuterated-alkoxyl" each refer to the chemical moiety wherein one carbon chain is bound to a deuterium.

The phrase "corresponding undeuterated compound" or "protonated analog" refers to a compound having identical chemical structure as a deuterated compound except that all hydrogen are present at their natural isotopic abundance percentages.

It will be recognized that some variation of natural isotopic abundance occurs in a synthesized compound depending upon the origin of chemical materials used in the synthesis. Thus, a preparation of a compound will inherently contain small amounts of deuterated isotopologues. The concentration of naturally abundant stable hydrogen and carbon isotopes, notwithstanding this variation, is small and immaterial as compared to the degree of stable isotopic substitution of deuterated compounds of this disclosure. In a deuterated compound of this disclosure, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in the compound.

The term "isotopic enrichment factor" as used herein means the ratio between the isotopic abundance and the natural abundance of a specified isotope.

In other embodiments, a compound of this disclosure has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The term "isotopologue" refers to a species that has the same chemical structure and formula as a specific compound of this invention, with the exception of the isotopic composition at one or more positions, e.g., H vs. D. Thus an isotopologue differs from a specific compound of this invention in the isotopic composition thereof.

When the term "independently selected" is used, the substituents being referred to (e.g., R groups, such as groups $R^1$ and $R^2$, or groups X and Y), can be identical or different. For example, both $R^1$ and $R^2$ can be substituted alkyls, or $R^1$ can be hydrogen and $R^2$ can be a substituted alkyl, and the like.

The term "treatment" as used herein covers any treatment of a disease and/or condition in an animal or mammal, particularly a human, and includes: (i) preventing a disease, disorder and/or condition from occurring in a person which can be predisposed to the disease, disorder and/or condition, or at risk for being exposed to an agent that can cause the disease, disorder, and/or condition; but, has not yet been diagnosed as having it; (ii) inhibiting the disease, disorder and/or condition, i.e., arresting its development; and (iii) relieving the disease, disorder and/or condition, i.e., causing regression of the disease, disorder and/or condition.

"Binding specificity" refers to the ability of a protein or other type of molecule capable of recognizing and interacting with a complementary site on another protein or other type of molecule.

The term "pharmacophore", as used herein, refers to a specific model or representation of a molecular moiety capable of exerting a selected biochemical effect, e g, inhibition of an enzyme, binding to a receptor, chelation of an ion, and the like. A selected pharmacophore can have more than one biochemical effect, e.g., can be an inhibitor of one enzyme and an agonist of a second enzyme. A therapeutic agent can include one or more pharmacophores, which can have the same or different biochemical activities.

The term "derivative" as used herein refers to a compound chemically modified so as to differentiate it from a parent compound. Such chemical modifications can include, for example, replacement of hydrogen by an alkyl, acyl, or amino group. A derivative compound can be modified by, for example, glycosylation, pegylation, or any similar process that retains at least one biological or immunological function of the compound from which it was derived.

The term "hydrophilicity" is used in the common manner of the field as having an affinity for water; readily absorbing and/or dissolving in water.

The term "lipophilicity" is used in the common manner of the field as having an affinity for, tending to combine with, or capable of dissolving in lipids.

The term "amphipathicity", as used herein, describes a structure having discrete hydrophobic and hydrophilic regions. Thus, one portion of the structure interacts favorably with aqueous and other polar media, while another portion of the structure interacts favorably with non-polar media.

The term "solubility" as used herein, describes the maximum amount of solute that will dissolve in a given amount of solvent at a specified temperature.

The term "bioavailability" as used herein refers to the systemic availability (i.e., blood/plasma levels) of a given amount of compound administered to a subject. The term further encompasses the rate and extent of absorption of compound that reaches the site of action.

Where the compounds of the present invention have at least one asymmetric center, they may accordingly exist as enantiomers. Where the compounds possess two or more asymmetric centers, they may additionally exist as diastereoisomers. It is to be understood that all such stereoisomers and mixtures thereof in any proportion are encompassed within the scope of the present invention. Where the compounds possess geometrical isomers, all such isomers and mixtures thereof in any proportion are encompassed within the scope of the present invention. Where so indicated in the claims herein, if a single enantiomer of the potentially optically active heterocyclic compounds disclosed is desired, for either health or efficacy reasons, preferably it is present in an enantiomeric excess of at least about 80%, or at least about 90%, or at least about 95%, or at least about 98%, or at least about 99%, or at least about 99.5%.

Tautomers of the compounds of the invention are encompassed by the present application. Thus, for example, a carbonyl includes its hydroxyl tautomer.

Compounds of the Present Application

In one aspect, the present application discloses a compound of Formula I:

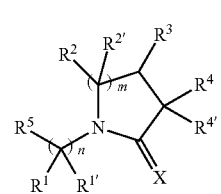

I or a pharmaceutically acceptable salt, ester, prodrug or solvate thereof, wherein: each of $R^1$, $R^{1'}$, $R^2$, $R^{2'}$, $R^3$, and $R^4$ is independently hydrogen, deuterium, optionally substituted alkyl, or optionally substituted deuterated-alkyl; or $R^2$ and $R^{2'}$ taken together form =O, =S, =CH$_2$, =CHD, or =CD$_2$; $R^{4'}$ is hydrogen or deuterium; $R^5$ is heterocycloalkyl or deuterated-heterocycloalkyl; X is CH$_2$, CDH, CD$_2$, NH, O or S; n is 0, 1, 2, 3, 4, or 5; and m is 1 or 2; with the proviso that the compound of Formula I comprises at least one carbon-bound deuterium.

In one embodiment, in the compound of Formula I, X is oxygen; and m is 1. In another embodiment, $R^2$ and $R^{2'}$ taken together form =O; and each of $R^3$ and $R^4$ is independently optionally substituted $C_1$-$C_6$ alkyl or optionally substituted deuterated-$C_1$-$C_6$ alkyl. In one variation of any of the disclosed aspects or embodiments, $R^5$ is morpholinyl, thiomorpholinyl, tetrahydro-2H-pyran, 1-methylpiperazinyl, piperidinyl, pyrrolidinyl, deuterated-morpholinyl, deuterated-thiomorpholinyl, deuterated-tetrahydro-2H-pyran, deuterated-1-methylpiperazinyl, deuterated-piperidinyl, or deuterated-pyrrolidinyl; and each of $R^1$ and $R^{1'}$ is independently hydrogen, deuterium, optionally substituted $C_1$-$C_4$ alkyl, or optionally substituted deuterated-$C_1$-$C_4$ alkyl.

In one embodiment, the present application discloses a compound of Formula IA:

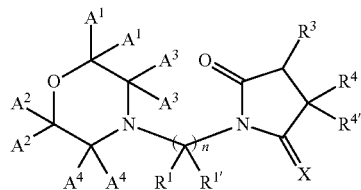

IA wherein each of $R^1$, $R^{1'}$, $R^4$ and $R^{4'}$ is independently hydrogen, deuterium, optionally substituted alkyl, or optionally substituted deuterated-alkyl; $R^3$ is hydrogen, optionally substituted alkyl, or optionally substituted deuterated-alkyl; each of $A^1$, $A^2$, $A^3$, $A^4$, and $R^{4'}$ is independently hydrogen or deuterium; and n is 0, 1, 2, 3, 4, or 5.

In another embodiment, n is 2; each of $R^1$ and $R^{1'}$ is hydrogen or deuterium; $R^3$ is methyl or deuterated-methyl; and $R^4$ is sec-butyl or deuterated-sec-butyl. In yet another embodiment, $R^5$ is a heterocycloalkyl bound via a heteroatom or a deuterated-heterocycloalkyl bound via a heteroatom; m is 2; and X is O. In a further embodiment, each of $R^2$ and $R^{2'}$ is independently hydrogen or deuterium; and $R^3$ is optionally substituted $C_1$-$C_4$ alkyl or optionally substituted deuterated-$C_1$-$C_4$ alkyl. In still another embodiment, $R^5$ is a nitrogen-bound morpholinyl, 1-methylpiperazinyl, piperidinyl, pyrrolidinyl, deuterated-morpholinyl, deuterated-1-methylpiperazinyl, deuterated-piperidinyl, or deuterated-pyrrolidinyl; and each of $R^1$ and $R^{1'}$ is independently hydrogen, deuterium, optionally substituted $C_1$-$C_4$ alkyl, or optionally substituted deuterated-$C_1$-$C_4$ alkyl.

In another embodiment, the present application discloses a compound of Formula IB:

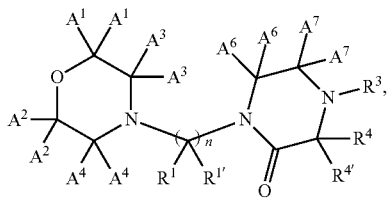

IB wherein each of $A^1$, $A^2$, $A^3$, $A^4$, $A^6$, $R^{4'}$, and $A^7$ is independently hydrogen or deuterium; and $R^4$ is hydrogen, deuterium, optionally substituted alkyl, or optionally substituted deuterated-alkyl.

In another embodiment, n is 2; each of $R^1$ and $R^{1'}$ is independently hydrogen or deuterium; $R^3$ is methyl or deuterated-methyl; and $R^4$ is sec-butyl or deuterated-sec-butyl.

In one aspect, the present application discloses a compound of Formula II:

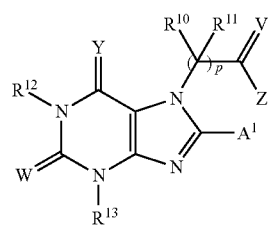

II or a pharmaceutically acceptable salt, ester, prodrug or solvate thereof, wherein: p is 0, 1, 2, 3, 4, 5, or 6; $A^1$ is hydrogen or deuterium; each of Y, V, and W is independently $CH_2$, CDH, $CD_2$, NH, O, or S; each of $R^{10}$ and $R^{11}$ is independently hydrogen, deuterium, optionally substituted alkyl, or optionally substituted deuterated-alkyl; each of $R^{12}$ and $R^{13}$ is independently hydrogen, —$NR^aR^b$, —OH, —C(=O)$OR^a$, —C(=O)$NHR^a$, —NHC(=O)$R^a$, —NHS(=O)$_2R^a$, optionally substituted alkyl, or optionally substituted deuterated-alkyl; each of $R^a$ and $R^b$ is independently hydrogen, optionally substituted alkyl, or optionally substituted deuterated-alkyl; and Z is an optionally substituted heterocycloalkyl, an optionally substituted deuterated-heterocycloalkyl, an optionally substituted heteroaryl, an optionally substituted deuterated-heteroaryl, or

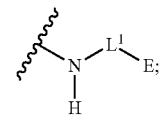

$L^1$ is a linking group selected from the group consisting of optionally substituted alkylene, optionally substituted deuterated-alkylene, optionally substituted cycloalkylene, optionally substituted deuterated-cycloalkylene, optionally substituted alkenylene, optionally substituted deuterated-alkenylene, optionally substituted arylene, optionally substituted deuterated-arylene, optionally substituted cycloalkenylene, and optionally substituted deuterated-cycloalkenylene; E is selected from the group consisting of:

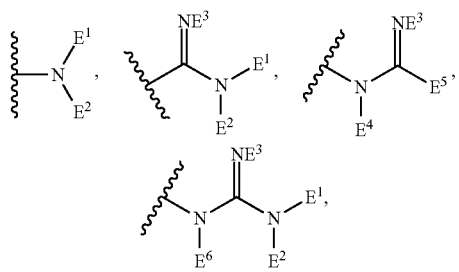

pyrrolidinyl, and deuterated-pyrrolidinyl; each of $E^1$, $E^2$, $E^4$, $E^5$, and $E^6$ independently is selected from the group consisting of hydrogen, optionally substituted alkyl, optionally substituted deuterated-alkyl, optionally substituted cycloalkyl, optionally substituted deuterated-cycloalkyl, optionally substituted aryl, optionally substituted deuterated-aryl, optionally substituted arylalkyl, and optionally substituted deuterated-arylalkyl; each $E^3$ is independently selected from the group consisting of hydrogen, hydroxyl, optionally substituted alkyl, optionally substituted deuterated-alkyl, optionally substituted aryl, optionally substituted deuterated-aryl, acyloxyl, alkoxyl, and deuterated-alkoxyl; with the proviso that the compound of Formula II comprises at least one carbon-bound deuterium.

In one embodiment, p is 1, 2 or 3; each of Y, V, and W is oxygen; each of $R^{12}$ and $R^{13}$ is independently hydrogen, optionally substituted $C_1$-$C_4$ alkyl, or optionally substituted deuterated-$C_1$-$C_4$ alkyl; and Z is an optionally substituted nitrogen-bound heterocycloalkyl or an optionally substituted nitrogen-bound deuterated-heterocycloalkyl. In another embodiment, p is 1; each of $R^{10}$ and $R^{11}$ is hydrogen or deuterium; and each of $R^{12}$ and $R^{13}$ is independently $C_1$-$C_4$ alkyl or deuterated-$C_1$-$C_4$ alkyl.

In one embodiment, the present application discloses a compound of Formula IIA:

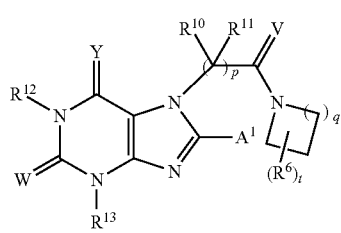

IIA or a pharmaceutically acceptable salt, ester, prodrug or solvate thereof, wherein: q is 1, 2, 3, or 4; t is an integer from 0 to 9; each of Y, V, and W is independently oxygen or sulfur; and $R^6$ is independently hydrogen, deuterium, —$NR^aR^b$, —OH, optionally substituted alkyl, or optionally substituted deuterated-alkyl. In one variation each of Y, V, and W is oxygen; q is 1; each of $R^{10}$ and $R^{11}$ is independently hydrogen, deuterium, $C_1$-$C_4$ alkyl, or deuterated-$C_1$-$C_4$ alkyl; and each of $R^{12}$ and $R^{13}$ is independently $C_1$-$C_4$ alkyl or deuterated-$C_1$-$C_4$ alkyl.

In another embodiment, each of $R^{10}$ and $R^{11}$ is independently hydrogen or deuterium; and each of $R^{12}$ and $R^{13}$ is independently methyl or deuterated-methyl. Alternately, each of $R^{10}$ and $R^{11}$ is independently hydrogen or deuterium; each of $R^{12}$ and $R^{13}$ is independently methyl or deuterated-methyl; and q is 2. In a further variation, t is 0.

In still a further embodiment, $L^1$ is

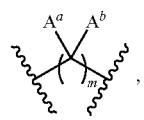

each of $A^a$ and $A^b$ independently is hydrogen or deuterium, and m is an integer from 1 to 8.

Still further the present application discloses a compound of Formula IIB:

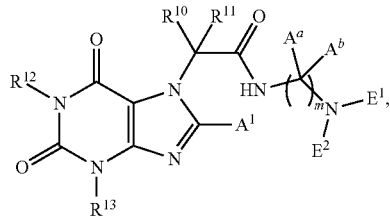

IIB or a pharmaceutically acceptable salt, ester, prodrug or solvate thereof.

The present application in particular discloses deuterated-2-(1,3-dimethyl-2,6-dioxo-2,3-dihydro-1H-purin-7(6H)-yl)-N-(3-(dimethylamino)propyl)acetamide, i.e., compounds having the following structure in a deuterated-form:

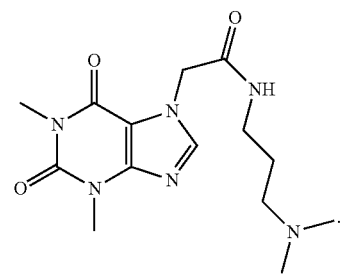

In one specific embodiment of Formula IIB, the compound has the following structure:

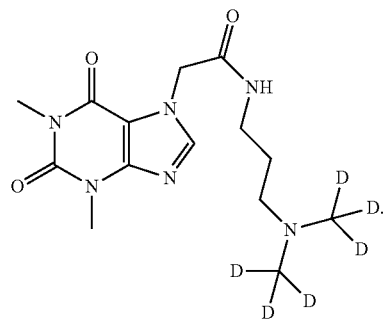

In one embodiment, the deuterated-2-(1,3-dimethyl-2,6-dioxo-2,3-dihydro-1H-purin-7(6H)-yl)-N-(3-(dimethylamino)propyl)acetamide has a structure of Formula IIB1:

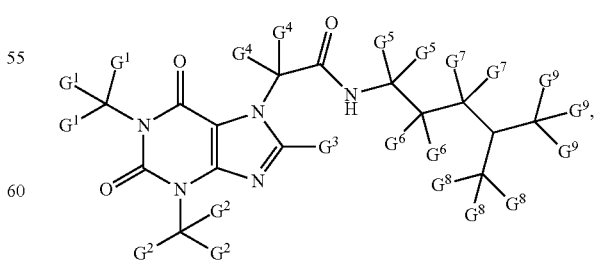

IIB1 wherein each of $G^1$, $G^2$, $G^3$, $G^4$, $G^5$, $G^6$, $G^7$, $G^8$, and $G^9$ is independently hydrogen or deuterium with the proviso that at least one of $G^1$, $G^2$, $G^3$, $G^4$, $G^5$, $G^6$, $G^7$, $G^8$, and $G^9$ is deuterium.

Further the present application discloses a compound of Formula IIIA:

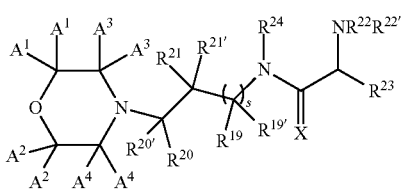

or a pharmaceutically acceptable salt, ester, prodrug or solvate thereof, wherein: X is $CH_2$, CDH, $CD_2$, NH, O or S; each of $A^1$, $A^2$, $A^3$, and $A^4$ is independently hydrogen or deuterium; s is 0, 1, 2, 3 or 4; each of $R^{19}$, $R^{19'}$, $R^{20}$, $R^{20'}$, $R^{21}$, $R^{21'}$, $R^{22}$, $R^{22'}$ and $R^{24}$ is independently hydrogen, deuterium, optionally substituted alkyl, or optionally substituted deuterated-alkyl; or $R^{20}$ and $R^{20'}$ taken together form =O, =S, $=CH_2$, =CDH, or $=CD_2$; or $R^{20}$ and $R^{21}$ taken together with the atoms to which they are attached form an optionally substituted cycloalkyl or optionally substituted deuterated-cycloalkyl; or $R^{20}$ and $R^{21}$ taken together with the atoms to which they are attached form an optionally substituted aryl or optionally substituted deuterated-aryl; or $R^{19}$ and $R^{20}$ taken together with the atoms to which they are attached form an optionally substituted cycloalkyl or optionally substituted deuterated-cycloalkyl; or $R^{19}$ and $R^{20}$ taken together with the atoms to which they are attached form an optionally substituted aryl or optionally substituted deuterated-aryl; and $R^{23}$ is optionally substituted alkyl, optionally substituted cycloalkyl or optionally substituted aryl or optionally substituted deuterated-aryl; or $R^{22}$ and $R^{23}$ taken together with the atoms to which they are attached form an optionally substituted heterocycloalkyl or optionally substituted deuterated-heterocycloalkyl; with the proviso that the compound of Formula IIIA comprises at least one carbon-bound deuterium.

In one embodiment, X is oxygen; s is 0; each of $R^{22}$ and $R^{22'}$ is hydrogen, deuterium, optionally substituted $C_1$-$C_6$ alkyl, or optionally substituted deuterated-$C_1$-$C_6$ alkyl. In another embodiment, each of $R^{20}$, $R^{20'}$, $R^{21}$, and $R^{21'}$ is independently hydrogen, deuterium, optionally substituted $C_1$-$C_4$ alkyl, or optionally substituted deuterated-$C_1$-$C_4$ alkyl; or $R^{20}$ and $R^{20'}$ taken together form =O. In still another embodiment $R^{20}$ and $R^{21}$ taken together with the atoms to which they are attached form an optionally substituted cycloalkyl or optionally substituted deuterated-cycloalkyl; or $R^{20}$ and $R^{21}$ taken together with the atoms to which they are attached form an optionally substituted aryl or optionally substituted deuterated-aryl. In another embodiment, s is 2; X is oxygen; $R^{19}$ and $R^{20}$ taken together with the atoms to which they are attached form an optionally substituted cycloalkyl or optionally substituted deuterated-cycloalkyl; or $R^{19}$ and $R^{20}$ taken together with the atoms to which they are attached form an optionally substituted aryl or optionally substituted deuterated-aryl.

The present application in particular discloses a compound of one of the following structures in a deuterated-form:

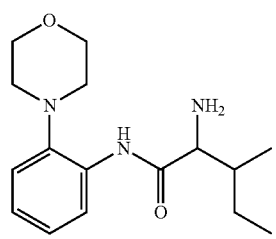

or

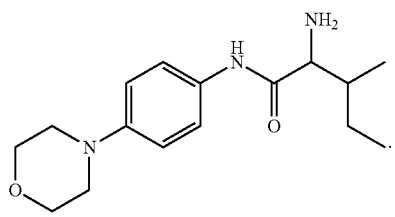

Still further, the present application in particular discloses a compound of one of the following structures in a deuterated-form:

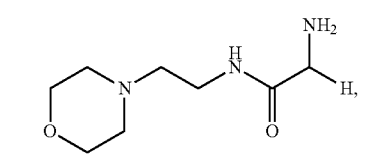 

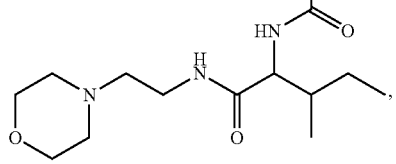

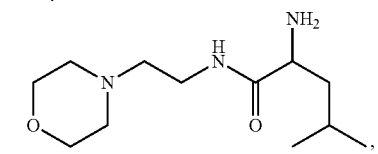

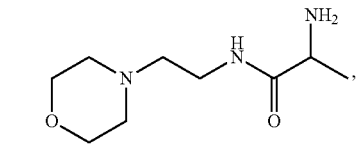

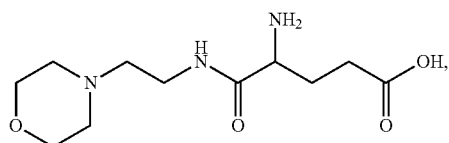

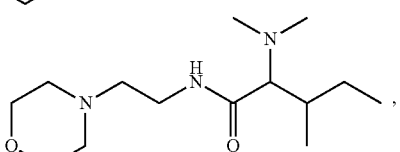

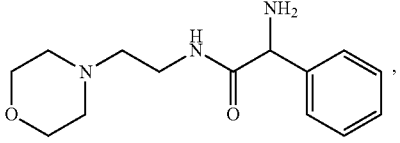

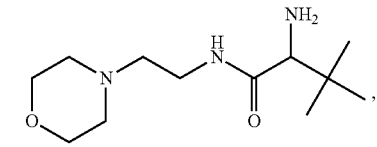

-continued

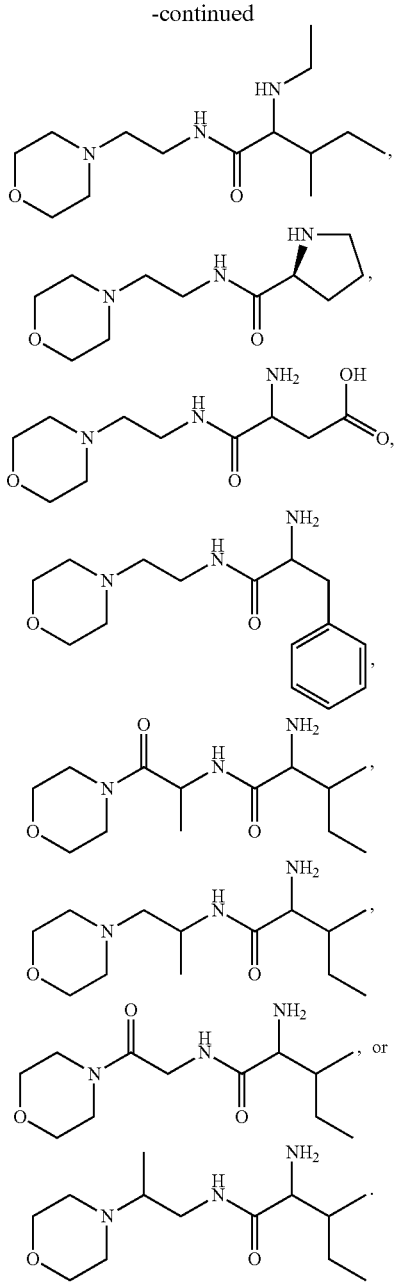

In another aspect, the present application discloses a compound of Formula IIIB:

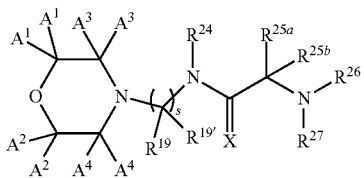
IIIB or a pharmaceutically acceptable salt, ester, prodrug or solvate thereof, wherein: X is $CH_2$, CDH, $CD_2$, NH, O or S; each of $A^1$, $A^2$, $A^3$, $A^4$, and $R^{25a}$ is independently hydrogen or deuterium; s is an integer from 1 to 8; each of $R^{19}$, $R^{19'}$, $R^{26}$, and $R^{27}$ is independently hydrogen, deuterium, optionally substituted alkyl, or optionally substituted deuterated-alkyl; $R^{24}$ is hydrogen, optionally substituted alkyl, or optionally substituted deuterated-alkyl; $R^{25b}$ is hydrogen, deuterium, halo, hydroxyl, alkoxy, deuterated-alkoxy, optionally substituted alkyl, optionally substituted deuterated-alkyl, optionally substituted cycloalkyl, optionally substituted deuterated-cycloalkyl, optionally substituted aryl, or optionally substituted deuterated-aryl; with the proviso that the compound of Formula IIIB comprises at least one carbon-bound deuterium. In one embodiment, X is oxygen and $R^{24}$ is hydrogen.

Further, the present application in particular discloses deuterated-2-amino-3-methyl-N-(2-morpholinoethyl)-pentanamide, i.e., compounds having the following structure in a deuterated-form:

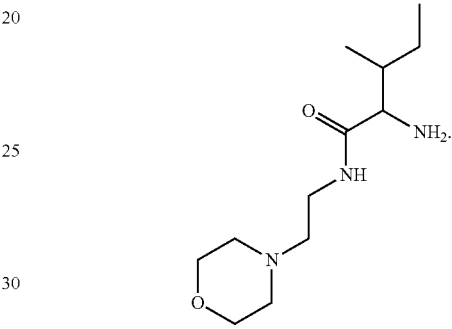

Such compounds further include a compound selected from the group consisting of: deuterated-(2S,3S)-2-amino-3-methyl-N-(2-morpholinoethyl)-pentanamide; deuterated-(2R,3R)-2-amino-3-methyl-N-(2-morpholinoethyl)-pentanamide; deuterated-(2R,3S)-2-amino-3-methyl-N-(2-morpholinoethyl)-pentanamide; deuterated-(2S,3R)-2-amino-3-methyl-N-(2-morpholinoethyl)-pentanamide; and a mixture thereof; or a pharmaceutically acceptable salt, solvate, ester, or prodrug thereof. (see Scheme A for the protonated analogs of these compounds).

Scheme A:

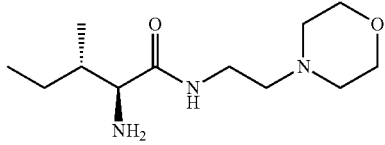 [SMILES: CC[C@H](C)[C@H](N)C(=O)NCCN1CCOCC1]

(2S,3S)-2-amino-3-methyl-N-(2-morpholinoethyl) pentanamide

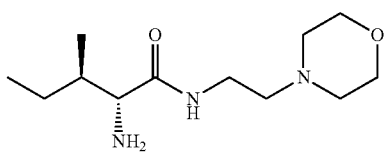 [SMILES: CC[C@@H](C)[C@@H](N)C(=O)NCCN1CCOCC1]

(2R,3R)-2-amino-3-methyl-N-(2-morpholinoethyl)
pentanamide

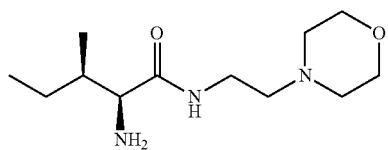 [SMILES: CC[C@@H](C)[C@H](N)C(=O)NCCN1CCOCC1]

(2S,3R)-2-amino-3-methyl-N-(2-morpholinoethyl)
pentanamide

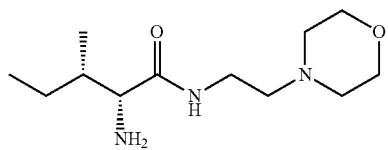

(2R,3S)-2-amino-3-methyl-N-(2-morpholinoethyl)
pentanamide

In one embodiment, the deuterated-2-amino-3-methyl-N-(2-morpholinoethyl)-pentanamide has a structure of Formula IIIA1:

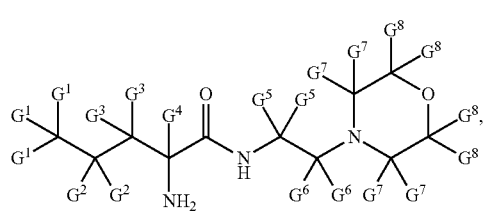

wherein each of $G^1$, $G^2$, $G^3$, $G^4$, $G^5$, $G^6$, $G^7$, and $G^8$ is independently hydrogen or deuterium with the proviso that at least of $G^1$, $G^2$, $G^3$, $G^4$, $G^5$, $G^6$, $G^7$, and $G^8$ is deuterium.

In one embodiment of the compound of Formula IIIA1, one, two, or three of $G^1$ is deuterium. Each of $G^2$, $G^3$, $G^4$, $G^5$, $G^6$, $G^7$, and $G^8$ is independently hydrogen or deuterium. When one or two $G^1$ is deuterium, each of the remaining $G^1$ is hydrogen.

In another embodiment of Formula IIIA1, one or two $G^2$ is deuterium. In another embodiment, one or two $G^3$ is deuterium. Each of $G^1$, $G^3$, $G^4$, $G^5$, $G^6$, $G^7$, and $G^8$ is independently hydrogen or deuterium. When one of $G^2$ is deuterium, the other $G^2$ is hydrogen.

In another embodiment of Formula IIIA1, one or two $G^3$ is deuterium. Each of $G^1$, $G^2$, $G^4$, $G^5$, $G^6$, $G^7$, and $G^8$ is independently hydrogen or deuterium. When one of $G^3$ is deuterium, the other $G^3$ is hydrogen.

In another embodiment of Formula IIIA1, $G^4$ is deuterium. Each of $G^1$, $G^2$, $G^3$, $G^5$, $G^6$, $G^7$, and $G^8$ is independently hydrogen or deuterium.

In another embodiment, one or two $G^5$ is deuterium. Each of $G^1$, $G^2$, $G^3$, $G^4$, $G^6$, $G^7$, and $G^8$ is independently hydrogen or deuterium. When one of $G^5$ is deuterium, the other $G^5$ is hydrogen.

In another embodiment of Formula IIIA1, one or two $G^6$ is deuterium. Each of $G^1$, $G^2$, $G^3$, $G^4$, $G^5$, $G^7$, and $G^8$ is independently hydrogen or deuterium. When one of $G^6$ is deuterium, the other $G^6$ is hydrogen.

In another embodiment of Formula IIIA1, one, two, three, or four of $G^7$ is deuterium. Each of $G^1$, $G^2$, $G^3$, $G^4$, $G^5$, $G^6$, and $G^8$ is independently hydrogen or deuterium. When two of $G^7$ is deuterium, the two deuterium atoms can be attached on the same or different carbon. When one, two, or three $G^7$ is deuterium, each of the remaining $G^7$ is hydrogen.

In another embodiment of Formula IIIA1, one, two, three, or four of $G^8$ is deuterium. Each of $G^1$, $G^2$, $G^3$, $G^4$, $G^5$, $G^6$, and $G^7$ is independently hydrogen or deuterium. When two of $G^8$ is deuterium, the two deuterium atoms can be attached on the same or different carbon. When one, two, or three $G^8$ is deuterium, each of the remaining $G^8$ is hydrogen.

In one specific embodiment, the compound of Formula IIIA1 has the following structure:

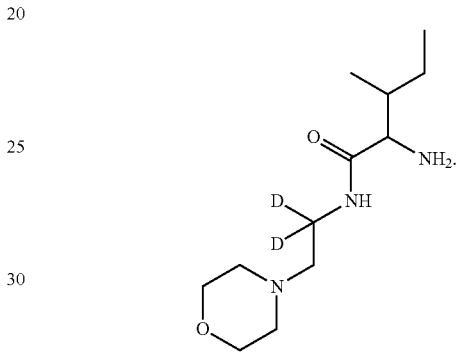

In another aspect, the present application discloses a compound of Formula IV:

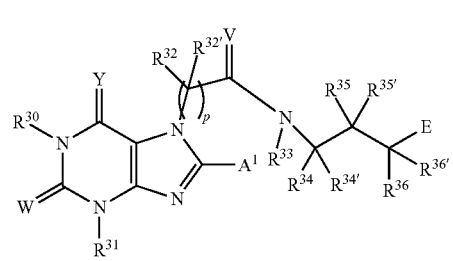

or a pharmaceutically acceptable salt, ester, prodrug or solvate thereof, wherein: p is 1, 2, 3, 4, 5, or 6; each of Y, V, and W is independently $CH_2$, CDH, $CD_2$, NH, O or S; $A^1$ is hydrogen or deuterium; each of $R^{30}$, $R^{31}$, $R^{32}$, $R^{32'}$ $R^{33}$, $R^{34}$, $R^{34'}$, $R^{35}$, $R^{35'}$, $R^{36}$, and $R^{36'}$ is independently hydrogen, deuterium, optionally substituted alkyl, or optionally substituted deuterium-alkyl; or $R^{34}$ and $R^{36}$ taken together with the atoms to which they are attached form an optionally substituted carbocyclic ring or optionally substituted deuterated-carbocyclic ring; E is —$CHR^cR^d$, —$CDR^cR^d$, —$NR^cR^d$, —$OR^c$, or —$SR^c$; and each of $R^c$ and $R^d$ is independently hydrogen, deuterium, optionally substituted deuterated-alkyl, or optionally substituted alkyl; or $R^c$ and $R^d$ taken together with the nitrogen atom to which they are attached form an optionally substituted heterocyclic ring or optionally substituted deuterated-heterocyclic ring; or $R^c$ and $R^d$ taken together with the carbon atom to which they are attached form an optionally substituted carbocyclic ring or optionally substituted deuterated-carbocyclic ring; with the proviso that the compound of Formula IV comprises at least one carbon-bound deuterium.

In one embodiment, p is 1, 2, or 3; each of Y, V, and W is oxygen or sulfur; each of $R^{32}$, $R^{32'}$ $R^{33}$, $R^{34}$, $R^{34'}$, $R^{35}$, $R^{35'}$, and $R^{36'}$ is independently hydrogen or deuterium; each of $R^{30}$ and $R^{31}$ is independently optionally substituted $C_1$-$C_4$ alkyl; and E is —$OR^c$ or —$SR^c$. In another embodiment, p is 1, 2, or 3; each of Y, V, and W is oxygen or sulfur; each of $R^{30}$ and $R^{31}$ is independently optionally substituted $C_1$-$C_4$ alkyl or optionally substituted deuterated-$C_1$-$C_4$ alkyl; each of $R^{32}$, $R^{32'}$ $R^{33}$, $R^{34}$, $R^{34'}$, $R^{35}$, $R^{35'}$, $R^{36}$, and $R^{36'}$ is independently hydrogen, deuterium, optionally substituted $C_1$-$C_4$ alkyl, or optionally substituted deuterated-$C_1$-$C_4$ alkyl; and E is —$NR^cR^d$ and $R^c$ and $R^d$ taken together with the nitrogen atom to which they are attached form an optionally substituted heterocycloalkyl or optionally substituted deuterated-heterocycloalkyl. In a further embodiment E is —$NR^cR^d$ and each of $R^c$ and $R^d$ is independently hydrogen, optionally substituted alkyl, or optionally substituted deuterated-alkyl. In another embodiment, $R^{34}$ and $R^{36}$ taken together with the atoms to which they are attached form an optionally substituted cycloalkyl or optionally substituted deuterated-cycloalkyl; or $R^{34}$ and $R^{36}$ taken together with the atoms to which they are attached form an optionally substituted aryl or optionally substituted deuterated-aryl.

The present application in particular discloses a compound of one of the following structures in a deuterated-form:

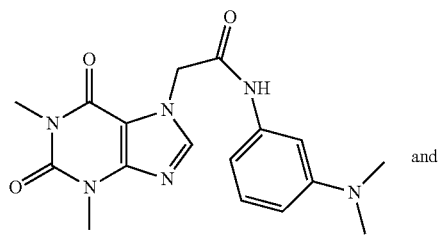

and

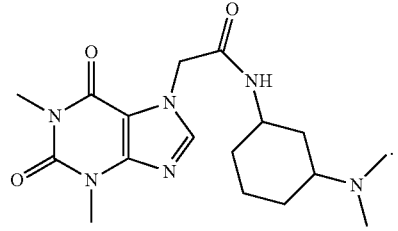

Still further, the present application in particular discloses a compound of one of the following structures in a deuterated-form:

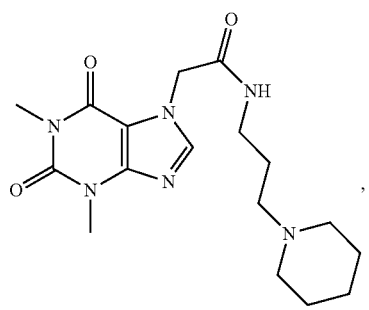

,

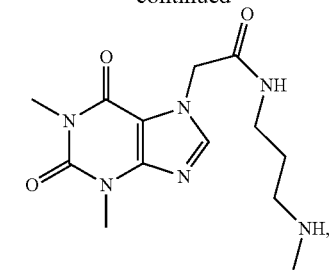

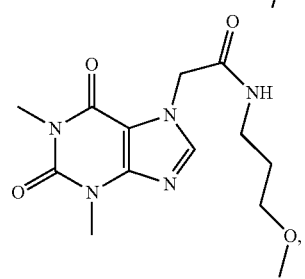

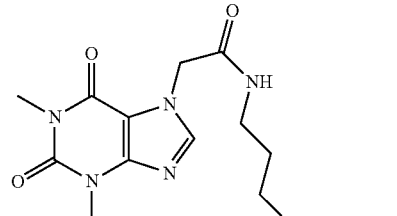

and

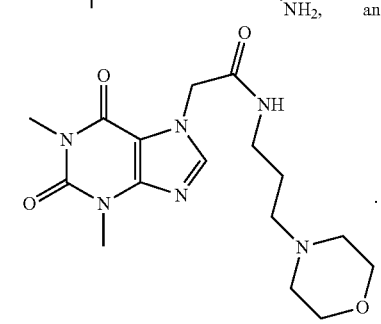

In another set of embodiments, a compound disclosed herein is isolated or purified, e.g., the compound is present at a purity of at least 50% by weight (e.g., at least 55%, 60%, 65%, 70%, 75%, 80%, 85%, 90%, 95%, 97%, 98%, 98.5%, 99%, 99.5% or 99.9%) of the total amount of isotopologues present. Thus, in some embodiments, a composition comprising a compound can include a distribution of isotopologues of the compound, provided at least 50% of the isotopologues by weight are the recited compound.

In some embodiments, any position in the compound designated as having D has a minimum deuterium incorporation of at least 45% (e.g., at least 52.5%, at least 60%, at least 67.5%, at least 75%, at least 82.5%, at least 90%, at least 95%, at least 97%, at least 99%, or at least 99.5%) at the designated position(s) of the compound o. Thus, in some embodiments, a composition comprising a compound can include a distribution of isotopologues of the compound, provided at least 45% of the isotopologues include a D at the designated position(s).

In some embodiments, a compound is "substantially free of" other isotopologues of the compound, e.g., less than 50%, less than 25%, less than 10%, less than 5%, less than 2%, less than 1%, or less than 0.5% of other isotopologues are present.

Since the p75 receptor is upregulated in various pathological states, the deuterated compounds disclosed herein can also be linked to molecular markers that can be detected by imaging or other modalities. Such conjugates can be prepared according to synthetic methods known to those of skill in the art and applied in diagnostic strategies designed to detect such pathological states.

The aforementioned individual compounds or mixtures can be used for treating a wide range of conditions and diseases described herein.

In one aspect, there is provided pharmaceutical compositions comprising a pharmaceutically acceptable diluent or carrier and a compound of Formula I, IA, IB, II, IIA, IIB IIIA, IIIB or IV or a pharmaceutically acceptable salt, ester, prodrug or solvate thereof. In another aspect, there is provided a method for the treatment of disorders involving degeneration or dysfunction of cells expressing p75 comprising administering to a patient in need of such treatment a compound of Formula, IA, IB, II, IIA, IIB IIIA, IIIB or IV or a pharmaceutically acceptable salt, ester, solvate or prodrug thereof or a stereoisomer of 2-amino-3-methyl-N-(2-morpholinoethyl)-pentanamide. In one embodiment, the disorder is a neurodegenerative disorder. In another embodiment, the disorder is selected from the group consisting of Alzheimer's disease, Huntington's disease, Pick's disease, amyotrophic lateral sclerosis, epilepsy, Parkinson's disease, spinal cord injury, stroke, hypoxia, ischemia, brain injury, diabetic neuropathy, peripheral neuropathy, nerve transplantation, multiple sclerosis, and peripheral nerve injury. In another embodiment, the disorder is hair loss.

In another aspect, there is provided a method for activating p75 receptors comprising contacting a cell containing a p75 receptor with a compound of Formula, IA, IB, II, IIA, IIB IIIA, IIIB or IV or a pharmaceutically acceptable salt, ester, solvate or prodrug thereof or a stereoisomer of 2-amino-3-methyl-N-(2-morpholinoethyl)-pentanamide.

Compounds of Formula, IA, IB, II, IIA, IIB IIIA, IIIB or IV or a pharmaceutically acceptable salt, ester, solvate or prodrug thereof or a stereoisomer of 2-amino-3-methyl-N-(2-morpholinoethyl)-pentanamide as disclosed herein that target p75 receptors expressed by neurons can be used to prevent loss of function, degeneration and/or death of neurons in a number of nervous system disorders including (but not limited to) Alzheimer's disease, Parkinson's disease, Huntington's disease, stroke, traumatic brain injury, spinal cord injury, epilepsy, multiple sclerosis, amyotrophic lateral sclerosis, neuropathies, myopathies and various forms of retinal degeneration. In one embodiment, compounds of the present application are used in the treatment of Alzheimer's disease.

Compounds of Formula, IA, IB, II, IIA, IIB IIIA, IIIB or IV or a pharmaceutically acceptable salt, ester, solvate or prodrug thereof or a stereoisomer of 2-amino-3-methyl-N-(2-morpholinoethyl)-pentanamide as disclosed herein that target p75 receptors expressed by oligodendrocytes can be used to prevent loss of function, degeneration and/or death of oligodendrocytes in a number of nervous system disorders including (and not limited to) multiple sclerosis, spinal cord injury and perinatal anoxia.

Outside of the nervous system, a number of cell populations express the p75 receptor. These include hair follicle cells, hepatic cells, vascular endothelial, vascular smooth muscle cells, cardiomyocytes. In addition, the p75 receptor is expressed by certain tumor cells such as those involved in breast or prostate cancer. Given this expression pattern, compounds of Formula, IA, IB, II, IIA, IIB IIIA, IIIB or IV or a pharmaceutically acceptable salt, ester, solvate or prodrug thereof or a stereoisomer of 2-amino-3-methyl-N-(2-morpholinoethyl)-pentanamide as disclosed herein that target p75 receptors can be used for the following indications: to prevent loss of hair follicle cells and thereby prevent hair loss; to prevent hepatic cirrhosis and promote liver regeneration; to regulate angiogenesis and promote neovascularization in the setting of diabetic wounds or other ischemic settings; to prevent cardiomyopathy by preventing myocardial cell loss or by stimulating growth of new cardiomyocytes either in the setting of ischemia or after myocardial infarction; and to inhibit tumor cell growth. In addition p75 is expressed by stem cells and is known to regulate stem cell growth; therefore, p75 ligands can be used to promote stem cell growth as part of a strategy to promote tissue and organ regeneration.

Formulations

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compounds can further be formulated for topical administration. Suitable topical formulations include one or more compounds in the form of a liquid, lotion, cream or gel. Topical administration can be accomplished by application directly on the treatment area. For example, such application can be accomplished by rubbing the formulation (such as a lotion or gel) onto the skin of the treatment area, or by spray application of a liquid formulation onto the treatment area.

In some formulations, bioimplant materials can be coated with the compounds so as to improve interaction between cells and the implant.

Formulations of the compounds can contain minor amounts of wetting or emulsifying agents, or pH buffering agents. The formulations comprising the compound can be a liquid solution, suspension, emulsion, tablet, pill, capsule, sustained release formulation, or powder.

The compounds can be formulated as a suppository, with traditional binders and carriers such as triglycerides.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Oral formulations can include standard carriers such as pharmaceutical grades of mannitol, lactose, starch, magnesium stearate, polyvinyl pyrrolidone, sodium saccharine, cellulose, magnesium carbonate, etc. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax maybe employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as *arachis* oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

The pharmaceutical formulations comprising the compounds of the present application can include an agent which controls release of the compound, thereby providing a timed or sustained release compound.

Carriers

Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions.

Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/ aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Salts

It is also to be understood that the disclosed compounds can further comprise pharmaceutically acceptable salts.

Such salts include, but are not limited to, pharmaceutically acceptable acid addition salts, pharmaceutically acceptable base addition salts, pharmaceutically acceptable metal salts, ammonium and alkylated ammonium salts.

Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like.

Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like.

Examples of metal salts include lithium, sodium, potassium, magnesium salts and the like.

Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

Therapeutic Use

The present application provides treatment of disorders involving degradation or dysfunction of cells expressing p75.

In another aspect, there is provided a method for activating p75 receptors comprising contacting a cell containing a p75 receptor. Additionally disclosed are methods for treating nervous system disorders including (but not limited to)

Alzheimer's disease, Parkinson's disease, Huntington's disease, stroke, traumatic brain injury, spinal cord injury, epilepsy, multiple sclerosis, amyotrophic lateral sclerosis, neuropathies, myopathies and various forms of retinal degeneration, based on the ability of the compounds of the present application to target p75 receptors expressed by neurons.

Additionally disclosed are methods for treating nervous system disorders including (and not limited to) multiple sclerosis, spinal cord injury and perinatal anoxia, based on the ability of the compounds of the present application to target p75 receptors expressed by oligodendrocytes.

Further disclosed are methods for treating diseases other than those of the nervous system, particularly preventing loss of hair follicle cells and thereby preventing hair loss; preventing hepatic cirrhosis and promote liver regeneration; to regulate angiogenesis and promote neovascularization in the setting of diabetic wounds or other ischemic settings; to prevent cardiomyopathy by preventing myocardial cell loss or by stimulating growth of new cardiomyocytes either in the setting of ischemia or after myocardial infarction; and to inhibit tumor cell growth. In addition p75 is expressed by stem cells and is known to regulate stem cell growth; therefore, p75 ligands can be used to promote stem cell growth as part of a strategy to promote tissue and organ regeneration.

The present application also provides methods of treating neurodegenerative and other disorders or conditions in a subject. More particularly, the methods of the present application involve administration of a compound having binding specificity for a $p75^{NTR}$ molecule in a subject to treat a neurodegenerative disorder or other disorder or condition. The compound can be administered in an amount effective to induce survival signaling and/or inhibit proNGF-induced cell death, which has been determined to be associated with neurodegenerative and other disorders.

The condition to be treated can be any condition which is mediated, at least in part, by binding of neurotrophins to $p75^{NTR}$. Such conditions include, but are not limited to, Alzheimer's disease, Huntington's disease, Pick's disease, amyotrophic lateral sclerosis, epilepsy, Parkinson's disease, spinal cord injury, stroke, hypoxia, ischemia, brain injury, diabetic neuropathy, peripheral neuropathy, nerve transplantation, multiple sclerosis, peripheral nerve injury, and hair loss.

The compounds having binding specificity for $p75^{NTR}$ can be used to treat neural degeneration, including preventing neurodegeneration such as, for example, neurodegeneration caused by chemotherapy and/or neurodegenerative disorders, as well as other conditions such as inducing hair follicle cell survival caused by, for example, chemotherapy.

The present application further provides for novel methods of facilitating cell survival. Representative cells include, but are not limited to, septal, hippocampal, cortical, sensory, sympathetic, motor neurons, hair follicle cells, progenitor, and stem cells. Generally, such cells include neurons, oligodendrocytes and hair follicle cells. Specifically, the methods comprise treating a cell with a compound having binding specificity for a $p75^{NTR}$ molecule, whereby the compound induces survival signaling and inhibits proNGF-induced cell death.

Administration

The present application discloses a method of administering compounds having binding specificity for $p75^{NTR}$ in order to ameliorate a condition mediated by $p75^{NTR}$ binding in a subject. The method can comprise the step of administering to a subject an effective amount of a compound having binding specificity for $p75^{NTR}$, such as any of the compounds disclosed herein.

As used herein, administering can be effected or performed using any of the various methods known to those skilled in the art. The compound can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed compounds can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form in which the compound is administered (e.g., syrup, elixir, capsule, tablet, solution, foams, emulsion, gel, sol) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The compound can also be used to coat bioimplantable materials to enhance neurite outgrowth, neural survival, or cellular interaction with the implant surface. The compounds and agents disclosed herein can be administered together with other biologically active agents, such as analgesics, anti-inflammatory agents, anesthetics and other agents which can control one or more symptoms or causes of a $p75^{NTR}$-mediated condition.

Additionally, administration can comprise administering to the subject a plurality of dosages over a suitable period of time. Such administration regimens can be determined according to routine methods, upon a review of the instant disclosure.

The compounds of the present application can be employed as the sole active agent in a pharmaceutical or can be used in combination (e.g., administered proximate in time to each other or even in the same formulation) with other active ingredients, e.g., neurotrophins, or other factors or drugs which can facilitate neural survival or axonal growth in neurodegenerative diseases, including but not limited to amyloid-β inhibitors, acetylcholinesterase inhibitors, butyrylcholinesterase inhibitors, and N-methyl-D-aspartate subtype of glutamate receptor antagonists.

Dosage

Compounds of the invention are generally administered in a dose of about 0.01 mg/kg/dose to about 100 mg/kg/dose. Alternately the dose can be from about 0.1 mg/kg/dose to about 10 mg/kg/dose; or about 1 mg/kg/dose to 10 mg/kg/dose. In some dosages, the compounds disclosed herein are administered at about 5 mg/kg/dose. Time release preparations may be employed or the dose may be administered in as many divided doses as is convenient. When other methods are used (e.g. intravenous administration), compounds are administered to the affected tissue at a rate from about 0.05 to about 10 mg/kg/hour, alternately from about 0.1 to about 1 mg/kg/hour. Such rates are easily maintained when these compounds are intravenously administered as discussed herein. Generally, topically administered formulations are administered in a dose of about 0.5 mg/kg/dose to about 10 mg/kg/dose range. Alternately, topical formulations are administered at a dose of about 1 mg/kg/dose to about 7.5 mg/kg/dose or even about 1 mg/kg/dose to about 5 mg/kg/dose.

A range of from about 0.1 to about 100 mg/kg is appropriate for a single dose. Continuous administration is appropriate in the range of about 0.05 to about 10 mg/kg. Topical administration is appropriate for conditions such as hair loss or wound revascularization.

Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) Cancer Chemother Rep. 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m$^2$.

Insofar as the compounds disclosed herein can take the form of a mimetic or fragment thereof, it is to be appreciated that the potency, and therefore dosage of an effective amount can vary. However, one skilled in the art can readily assess the potency of a compound of the type presently envisioned by the present application.

In settings of a gradually progressive nervous system disorder, compounds of the present application are generally administered on an ongoing basis. In certain settings administration of a compound disclosed herein can commence prior to the development of disease symptoms as part of a strategy to delay or prevent the disease. In other settings a compound disclosed herein is administered after the onset of disease symptoms as part of a strategy to slow or reverse the disease process and/or part of a strategy to improve cellular function and reduce symptoms. Compounds have been developed that cross the blood brain barrier and hence would be delivered by oral administration or by other peripheral routes. Compounds that do not cross the blood brain barrier are applied for targets outside of the central nervous system. For targets and tissues outside of the nervous system, compounds are applied in either acute or chronic settings by other oral or directed target administration such as by topical application.

It will be appreciated by one of skill in the art that dosage range will depend on the particular compound, and its potency. The dosage range is understood to be large enough to produce the desired effect in which the neurodegenerative or other disorder and the symptoms associated therewith are ameliorated and/or survival of the cells is achieved, but not be so large as to cause unmanageable adverse side effects. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art. The dosage can also be adjusted by the individual physician in the event of any complication. No unacceptable toxicological effects are expected when compounds disclosed herein are used in accordance with the present application.

An effective amount of the compounds disclosed herein comprise amounts sufficient to produce a measurable biological response. Actual dosage levels of active ingredients in a therapeutic compound of the present application can be varied so as to administer an amount of the active compound that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Further with respect to the methods of the present application, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the present application indicate effectiveness with respect to all vertebrate species which are to included in the term "subject." In this context, a vertebrate is understood to be any vertebrate species in which treatment of a neurodegenerative disorder is desirable. As used herein, the term "subject" includes both human and animal subjects. Thus, veterinary therapeutic uses are provided in accordance with the present application.

As such, the present application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

EXAMPLES

General Syntheses

Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M., Advanced Organic Chemistry, 6th ed., John Wiley and Sons, New York, N.Y.; and Larock R. C., Comprehensive Organic Transformations, Wiley-VCH Publishers, New York, 1999. All texts and references cited herein are incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, Protecting Groups in Organic Synthesis, 3rd edition, John Wiley & Sons, Inc. 1999.

The present deuterated-compounds can be prepared by synthetic methods well-known to one skilled in the art. For example, the deuterated-compounds can be prepared by modifying the synthesis of the corresponding undeuterated compounds. In some embodiments, certain starting materials or chemical reagents in the synthesis of the corresponding undeuterated compounds can be replaced with the deuterated starting materials or chemical reagents to make the deuterated compounds. In some specific embodiments of the present invention, the present deuterated compounds may be prepared by using deuterated isoleucine and/or deuterated alanine or its protected analog, such as isoleucine-$d_{10}$, i.e., $CD_3CD_2CD(CD_3)CD(NH_2)COOH$; $CD_3CD(NH_2)COOH$; $CD_3CH(NH_2)COOH$; $CD_3CD(ND_2)COOD$; and $CD_3CH(NH\text{-}t\text{-}BOC)COOH$; which are commercially available from Cambridge Isotope Laboratories. In some specific embodiments, deuterated starting materials or chemical reagents can be prepared by transformation of the undeuterated precursors. One common method of preparing deuterated compounds is by reduction of certain undeuterated precursors using deuterated reductive agents.

For example, 2,2,6,6,-tetradeuteropiperidine may be obtained by reduction of 2,6-dioxopiperidine or its N-protected analogs, for instance N-benzyl or N-4-methoxyphenyl, with agents such as $LiAlD_4$ or DIBAL-d (Kalvin D M and Woodward R D, Tetrahedron 1984 40: 3387). In another example, 2,3,3,4,5,5,6-Heptadeuteropiperidine can be conveniently obtained by dissolving metal reduction of pyridine in ethanol-d ($CH_3CH_2OD$) with sodium metal, under which conditions exchange of hydrogen for solvent deuterium occurs at the 3 and 5-positions (Vierhapper F W et al., J. Org. Chem. 1975 40: 2734). In yet another example, the readily available 2,6-dibromopyridine is subjected to halogen-deuterium exchange, for instance by metallation and deuterium oxide quench, or by catalytic reduction with deuterium gas (Yadav J S et al., Adv. Synth. Catal. 2004 346: 77; and Kirefu T, et al. J. Label. Compd. Radiopharm. 2001 44: 329), the resulting 2,6-dideuteriopyridine may be subjected to sodium/ethanol-d reduction as above to yield 2,2,3,3,4,5,5,6,6, nonadeuteropiperidine. In yet another example, 2,2,3, 3,4,4,5,5,6,6-decadeuteropiperidine can be obtained by analogous reducing metal reduction, or for instance by catalytic reduction under deuterium gas, starting from the readily commercially available pentadeuteropyridine (Aldrich Chemicals, Cambridge Isotope Laboratories, C/D/N Isotopes).

Synthesis of the examples of the deuterated compounds and the corresponding undeuterated compounds, such as Compounds 1 to 21, are illustrated in the general Schemes 1 to 6 as well as the specific schemes shown below. One skilled in the art can readily derive the synthesis of the present deuterated compounds from the following examples according to the methods discussed above.

Scheme 1

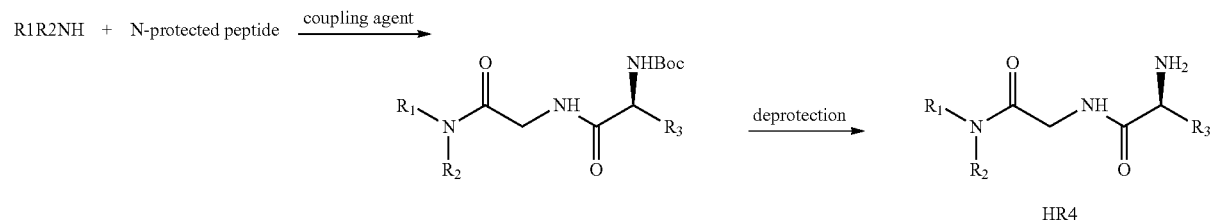

Scheme 2

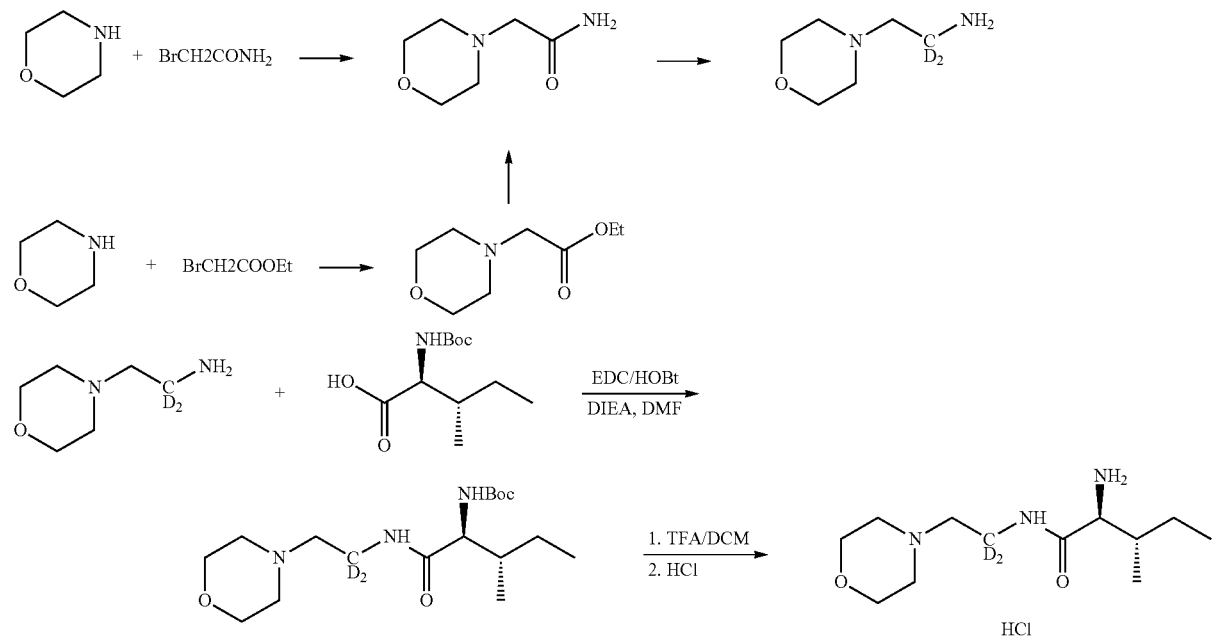

Generally the protection group for the amino acid is a Boc group. The coupling agent can be HATU, HBTU, EDC/HOBt, or DCC/DMAP. The deprotection reagent can be 4 M HCl in MeOH, 4M HCl in water, or TFA in DCM.

Generally, an amine or aniline is coupled with an N-protected amino acid and this coupled intermediate is deprotected to give a final compound or another intermediate. Exemplary N-protected amino acids that can be used as a starting material for some of the compounds disclosed herein include $CD_3CH(NH-t-BOC)COOH$ (purchased from Cambridge Isotope Laboratories) and $CD_3CD_2CD(CD_3)CD(NH-t-BOC)COOH$ ($CD_3CD_2CD(CD_3)CD(NH_2)COOH$ purchased from Cambridge Isotope Laboratories) The second intermediate can be further modified as necessary or directly go through a coupling-deprotection cycle one more time to give the final compound.

For those compounds deuterated at the amine in Scheme 1, such as a deuterated morpholine ring, Morpholine-2,2,3,3,5,5,6,6-$d_8$ is available from C/D/N Isotopes (Quebec, Canada).

Example 1

Preparation of Compound 1

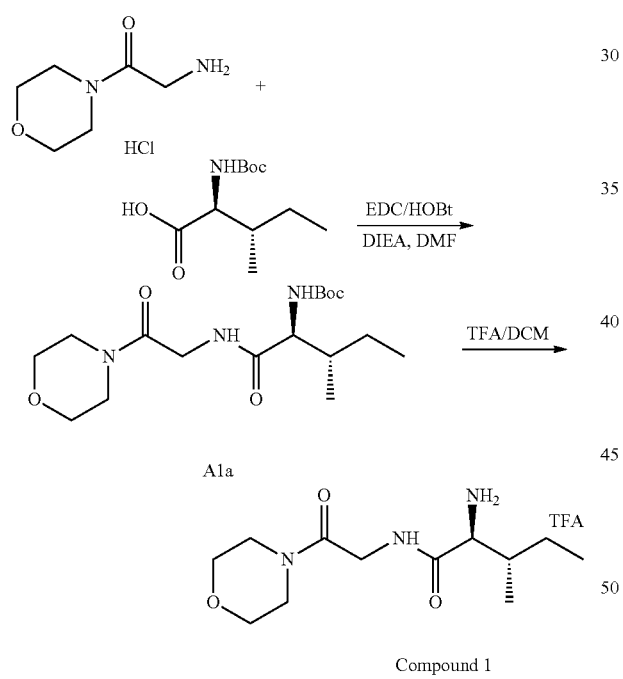

Ala

Compound 1

Example 2

Preparation of Compound 2

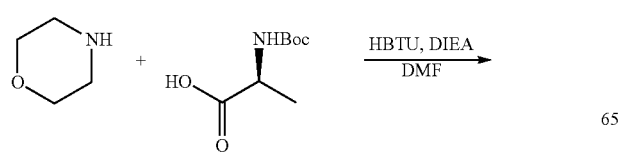

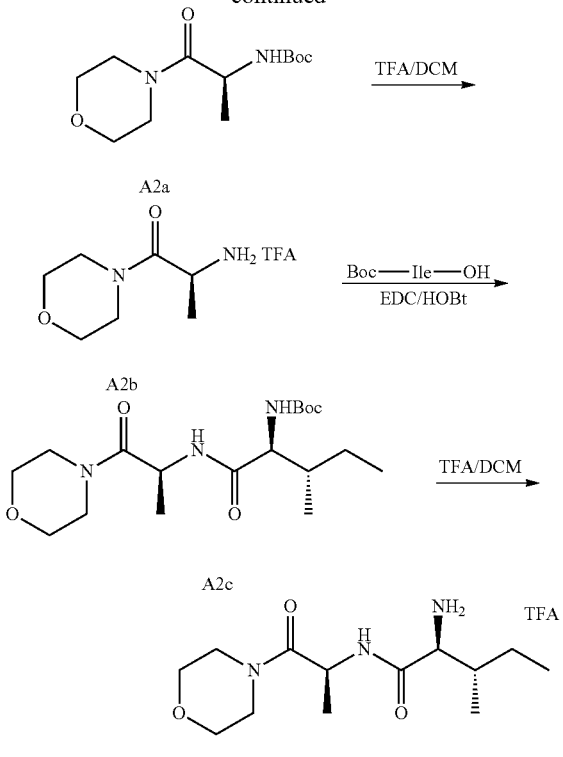

A2a

A2b

A2c

Compound 2

Example 3

Preparation of Compound 3

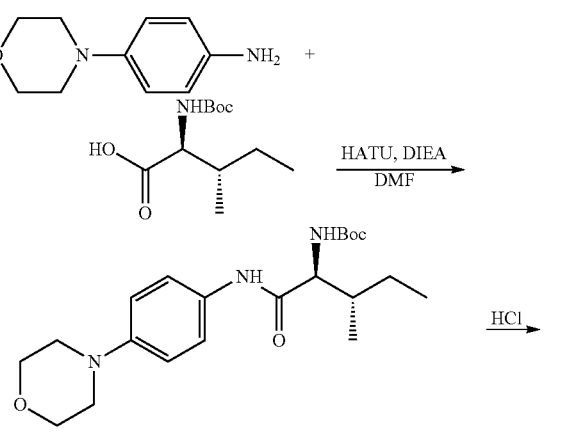

A3a

Compound 3

Example 4

Preparation of Compound 4

[Reaction scheme: 2-morpholinoaniline + Boc-protected (2S,3S)-2-amino-3-methylpentanoic acid, EDC/HOBt, DCM/DIEA → A4a; then HCl/MeOH → Compound 4 (·2 HCl)]

Example 5

Preparation of Compound 5

[Reaction scheme: 2-morpholino-1-propylamine + Boc-Ile-OH analog, EDC/HOBt, DCM/DIEA → A5a; then HCl → Compound 5 (·2 HCl)]

Example 6

Preparation of Compound 6

[Reaction scheme: morpholine + Boc-Ala-OH, HBTU, DIEA, DMF → A6a; BH₃–THF → A6b; HCl → A6c; Boc-Ile-OH, EDC/HOBt → A6d; HCl → Compound 6 (·2 HCl)]

Example 7

Preparation of Compound 7

[Reaction scheme: 4-(2-aminoethyl)morpholine + BrCH₂CH(OEt)₂, 70° C. →]

-continued
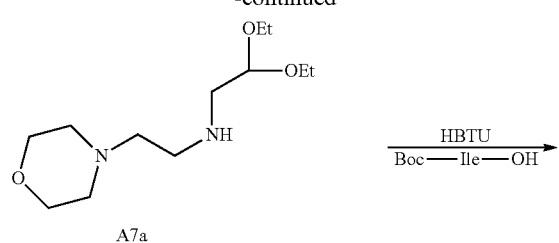
A7a
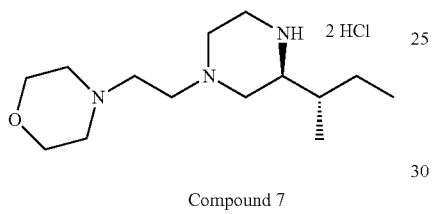
A7b
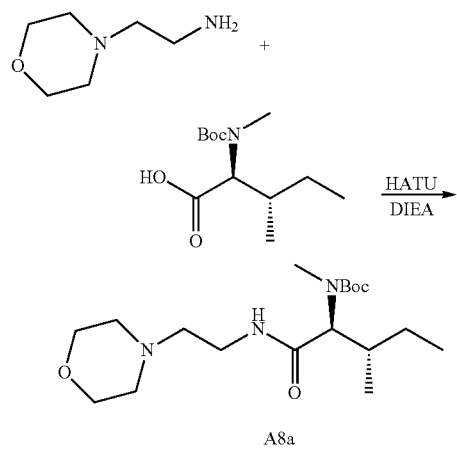
Compound 7
Example 8
Preparation of Compound 8
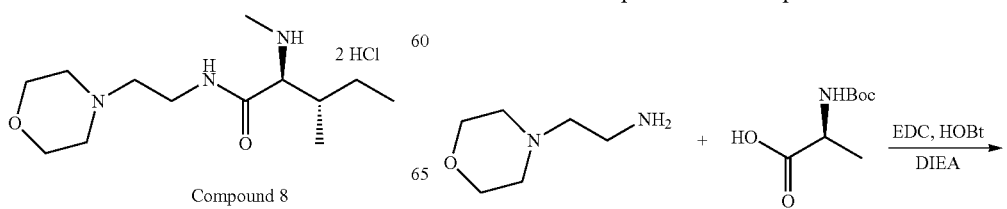
Example 9
Preparation of Compound 9
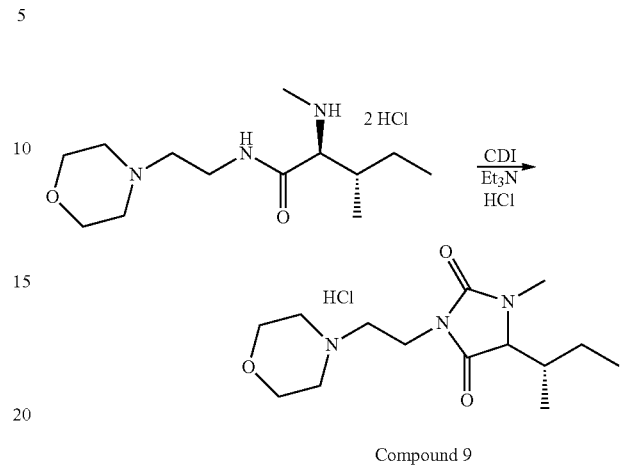
Compound 9
Example 10
Preparation of Compound 10
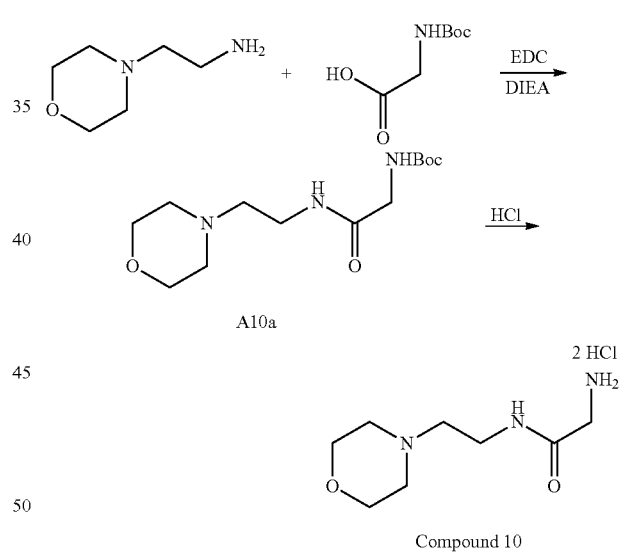
Compound 10
Example 11
Preparation of Compound 11

-continued

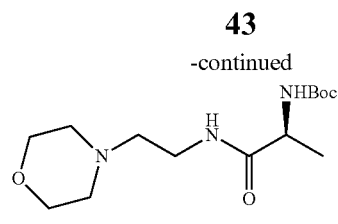

A11a

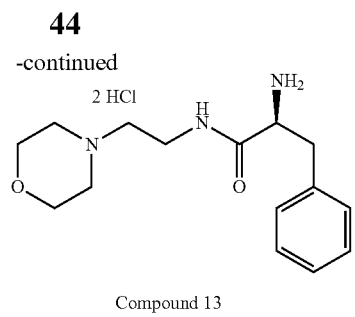

Compound 13

A number of compounds, including Compound 14, Compound 15, Compound 16, Compound 17, and Compound 18, can be prepared according to the method of preparation of Compound 13, substituting the appropriate starting materials.

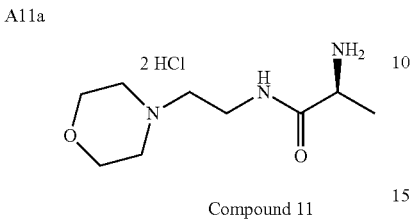

Compound 11

Example 12

Preparation of Compound 12

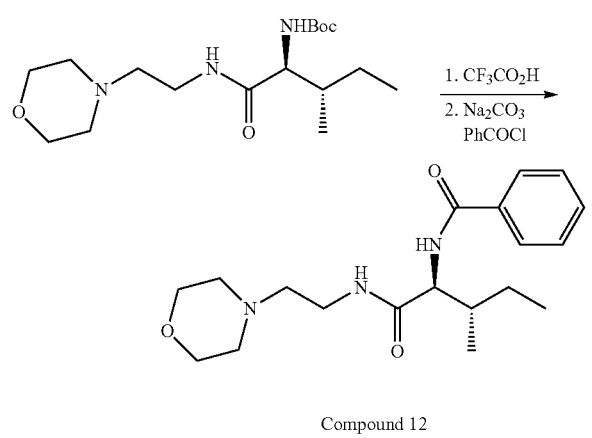

Compound 12

Example 13

Preparation of Compound 13

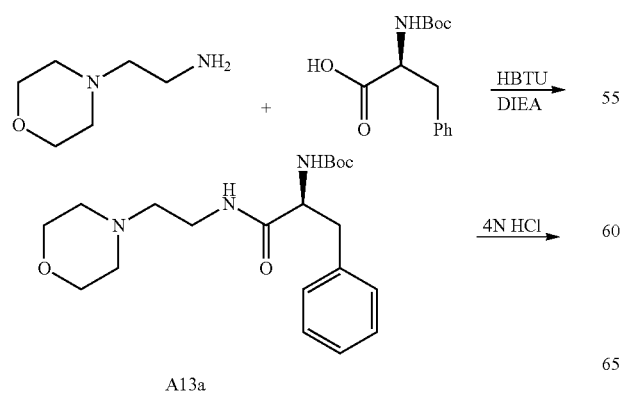

A13a

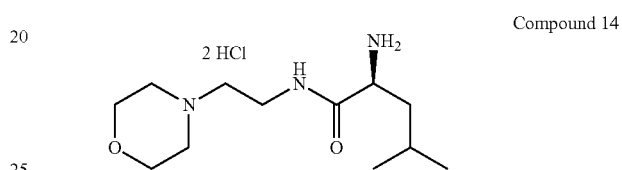

Compound 14

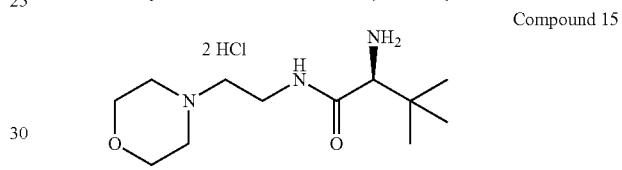

Compound 15

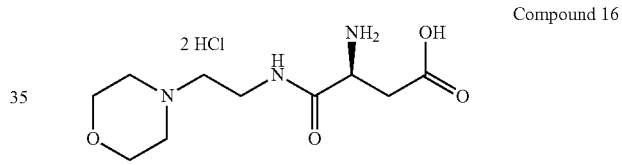

Compound 16

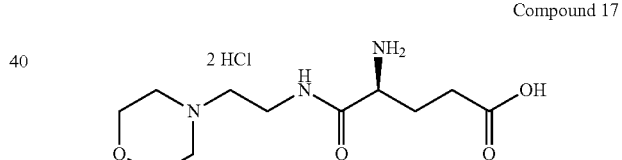

Compound 17

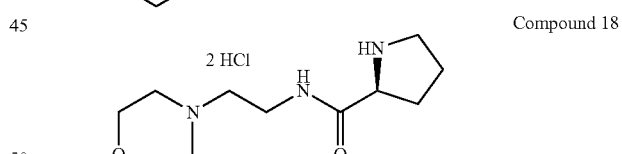

Compound 18

Example 19

Preparation of Compound 19

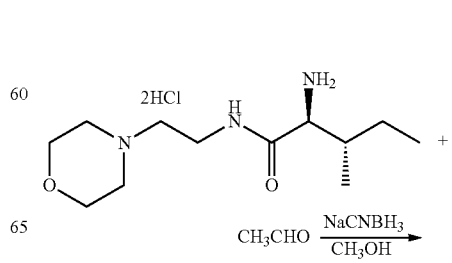

-continued

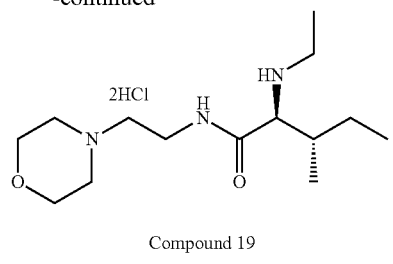

Compound 19

Example 20

Preparation of Compound 20

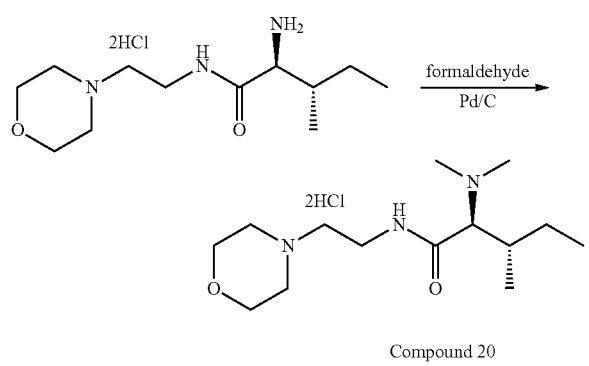

Compound 20

Example 21

Preparation of Compound 21

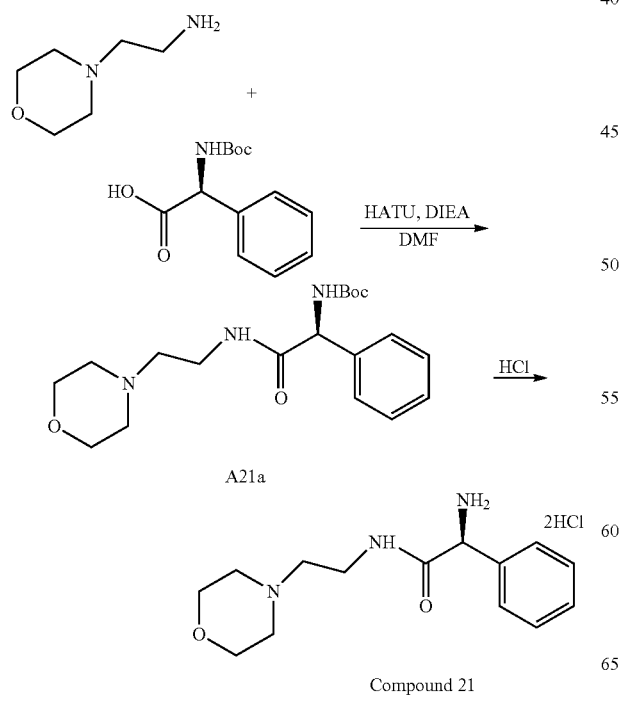

Compound 21

Preparation of analogs of a number of compounds of the present application is illustrated in the general Scheme 3 below:

Scheme 3

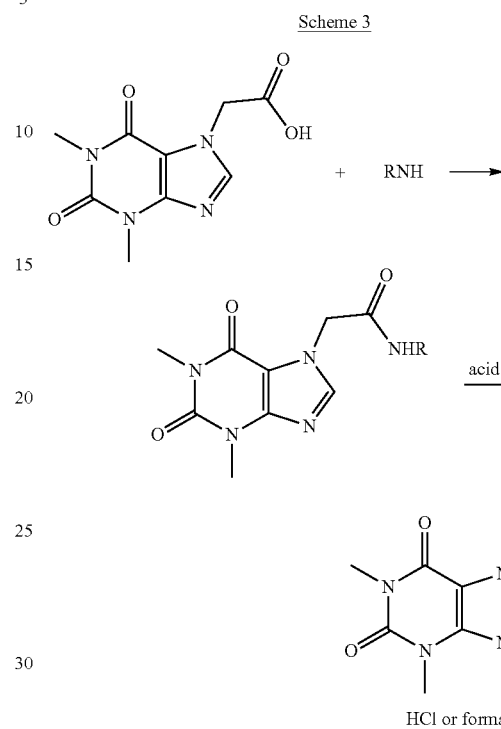

In such a synthesis strategy, the coupling agent can be HATU or HBTU. The acid used to remove a protection group such as Boc can be 4 M HCl in MeOH or 4M HCl in water.

Preparation of additional compounds of the present application can be illustrated in the general Scheme 4 below:

Scheme 4

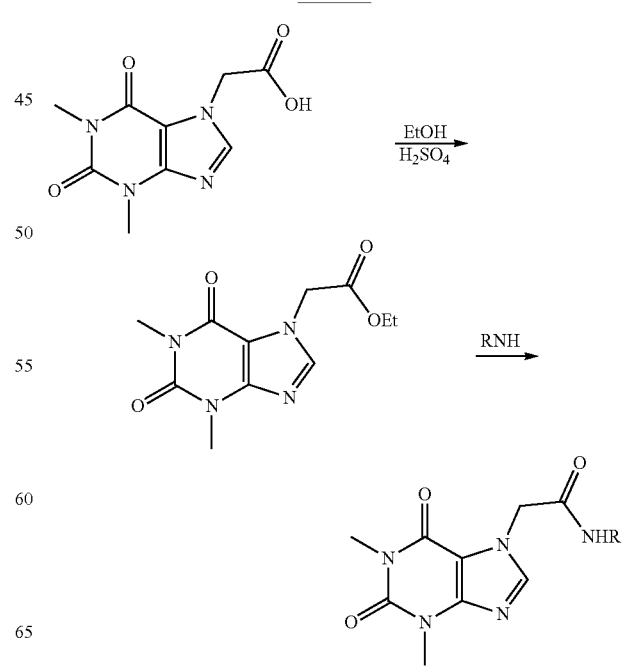

In this synthesis, the starting material acid is first converted to an ester. Then the ester is reacted with an amine to afford an amide compound. The amide compound may undergo further transformation, such as reductive amination, to afford the final compound.

Scheme 5

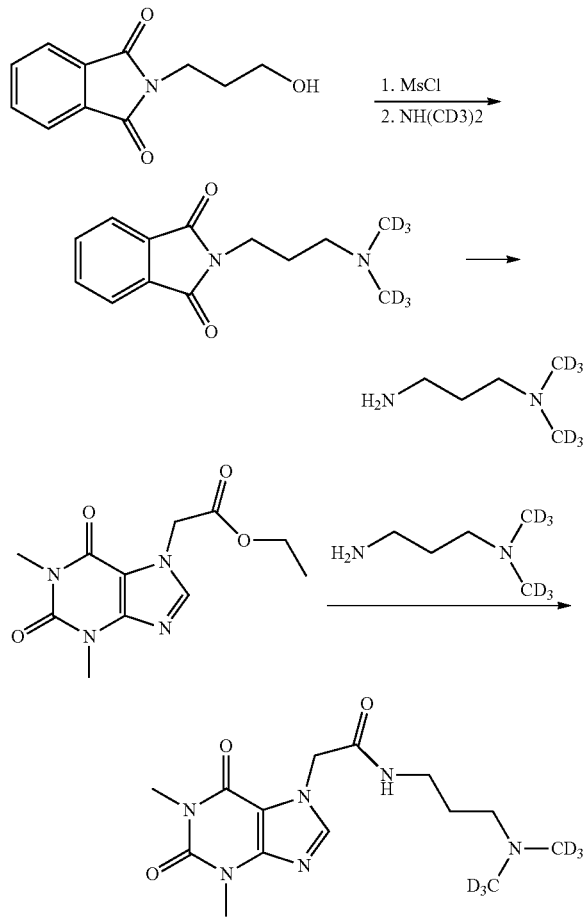

Example 22

Preparation of Compound 22

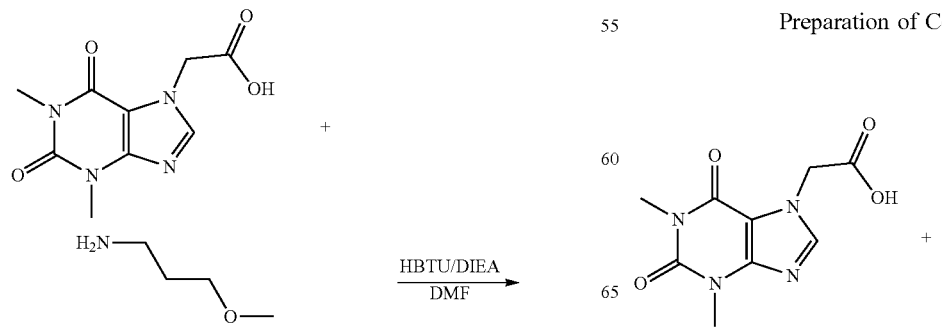

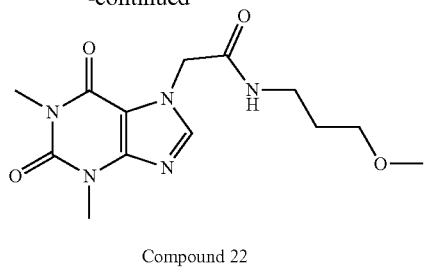

Compound 22

Example 23

Preparation of Compound 23

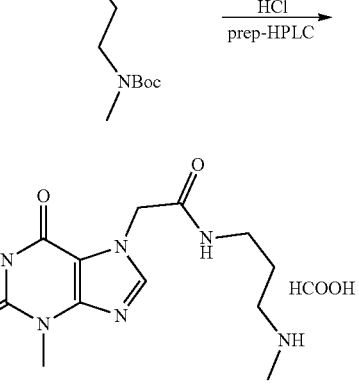

Example 24

Preparation of Compound 24

49
-continued
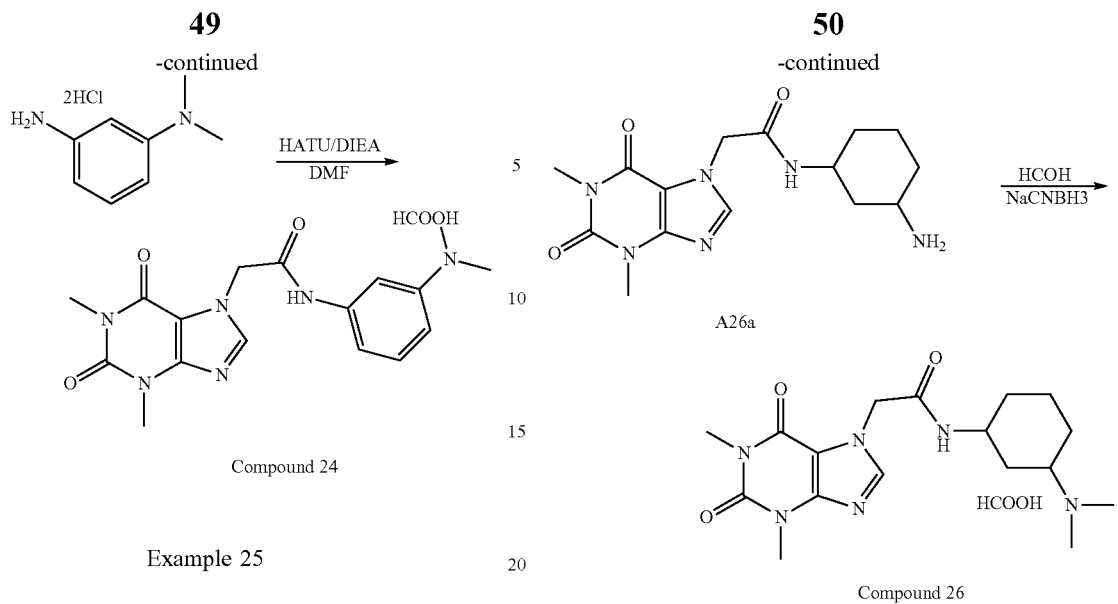
Compound 24
Example 25
Preparation of Compound 25
50
-continued
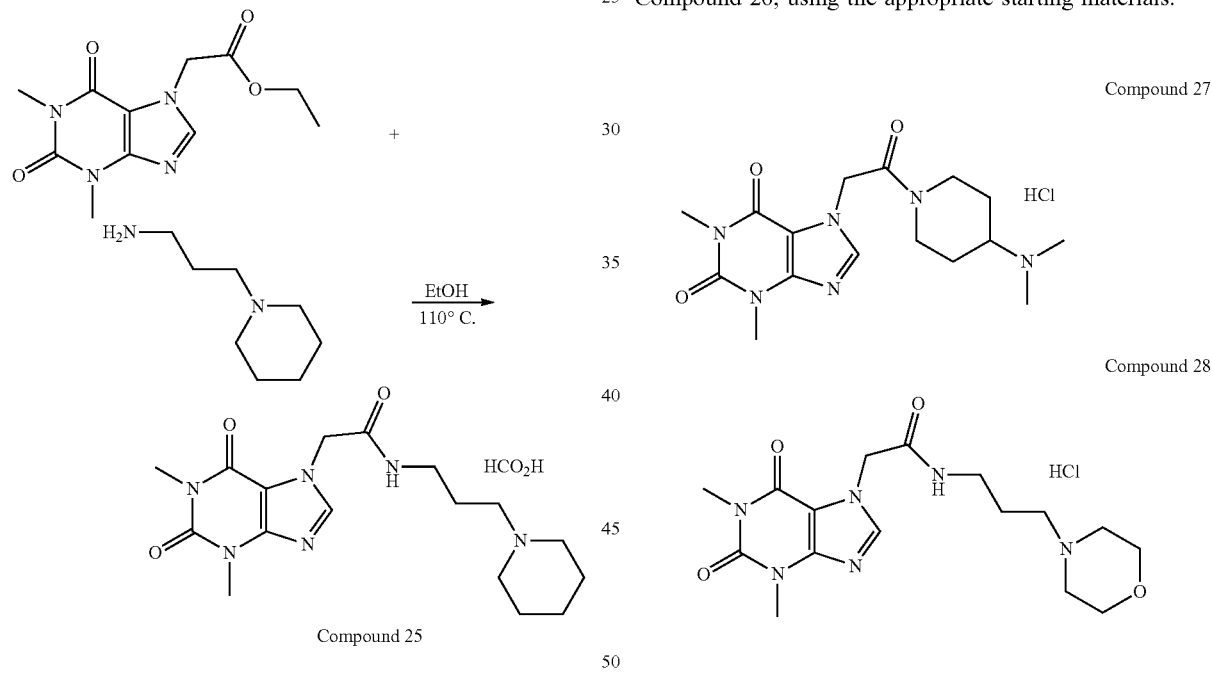
A26a
Compound 26
Compounds 27 and 28 can be prepared analogously to Compound 26, using the appropriate starting materials.
Compound 27
Compound 28
Example 29
Preparation of Compound 29
Example 26
Preparation of Compound 26
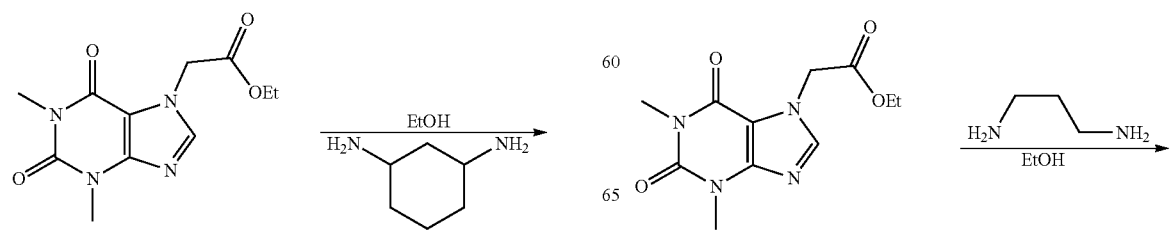

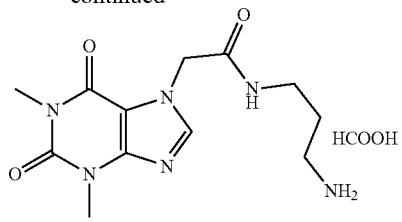

Compound 29

Example 30

Preparation of Compound 30

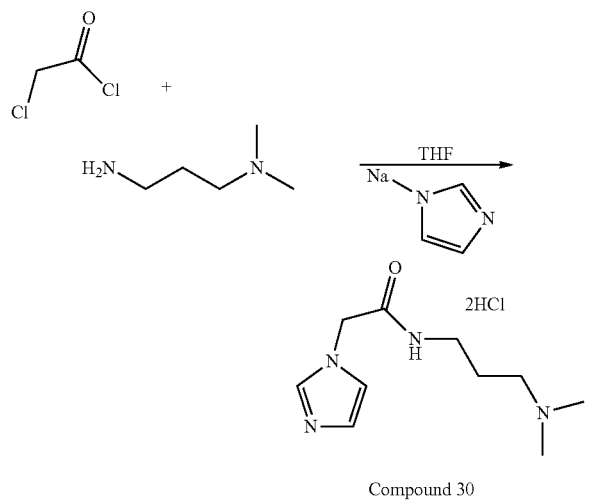

Compound 30

Example 31

Preparation of Compound 31

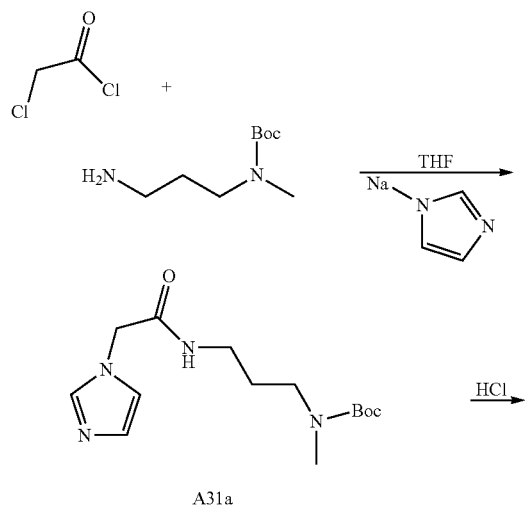

A31a

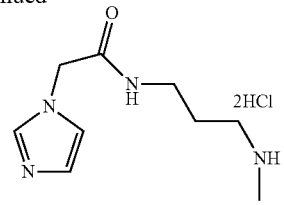

Compound 31

Example

Preparation of enantiomerically pure 2-amino-3-methyl-N-(2-morpholinoethyl)-pentanamide 2-amino-3-methyl-N-(2-morpholinoethyl)-pentanamide can be prepared by a method shown in Scheme 3 below. First, 2-aminoethanol (Compound 1E) is transformed to its derivative with a leaving group (Compound 2E). Examples of the leaving group include halides and alkoxy or other activated hydroxyl group. Second, Compound 2E reacts with morpholine at a neutral or basic condition to yield 2-morpholinoethanamine (Compound 3E). The aforementioned two steps may also be performed continuously as one step with Compound 2E being generated in situ. For example, Compound 3E can be prepared from Compound 1E directly through a Mitsunobu reaction wherein the hydroxyl group of Compound 1E is activated by diethyl azodicarboxylate (DEAD) before morpholine is added. The final product, 2-amino-3-methyl-N-(2-morpholinoethyl)-pentanamide (Compound 5E), can be obtained by coupling 2-morpholinoethanamine with 2-amino-3-methylpentanoic acid (Compound 4E) via a peptide coupling agent. Examples of the peptide coupling agent include 1,1'-carbonyldiimidazole (CDI), hydroxybenzotriazole (HOBT), 1,3-dicyclohexylcarbodiimide (DCC), 1-hydroxybenzo-7-azatriazole (HOAt), and the like.

Scheme 6:

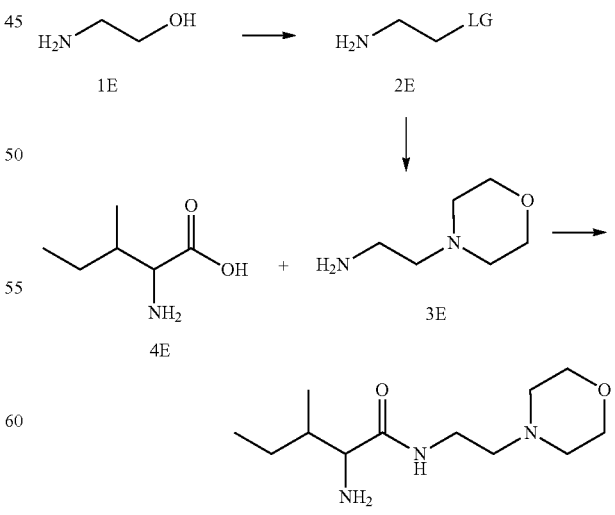

LG: a leaving group

A chiral 2-amino-3-methyl-N-(2-morpholinoethyl)-pentanamide (Compound 5E) can be obtained by using the corresponding chiral 2-amino-3-methylpentanoic acid (Compound 4E) in the above coupling step. For example, (2S,3S)-2-amino-3-methyl-N-(2-morpholinoethyl)-pentanamide; (2R,3R)-2-amino-3-methyl-N-(2-morpholinoethyl)-pentanamide; (2R,3S)-2-amino-3-methyl-N-(2-morpholinoethyl)-pentanamide; and (2S,3R)-2-amino-3-methyl-N-(2-morpholinoethyl)-pentanamide can be obtained by using (2S,3S)-2-amino-3-methylpentanoic acid, i.e., L-isoleucine; (2R,3R)-2-amino-3-methylpentanoic acid, i.e., D-isoleucine; (2R,3S)-2-amino-3-methylpentanoic acid, i.e., D-alloisoleucine; and (2S,3R)-2-amino-3-methylpentanoic acid, i.e., L-alloisoleucine, respectively.

The chiral purity, also known as, enantiomeric excess or EE, of a chiral Compound 5E can be determined by any method known to one skilled in the art. For example, a chiral Compound 5E can be hydrolyzed to Compound 3E and the corresponding chiral Compound 4E. Then, the chiral Compound 4E obtained through hydrolysis can be compared with a standard chiral sample of Compound 4E to determine the chiral purity of the chiral Compound 5E. The determination can be conducted by using a chiral HPLC.

Example

Measurement of Activity Relative to BDNF

Compounds of the present application are tested for their ability to prevent the degeneration of hippocampal neurons as described in Massa et al *J Neurosci.* (2006) 26(20):5288-300. In brief, hippocampal neurons are isolated from embryological day 16 mice and seeded in 96-well tissue culture plates under conditions in which they degenerated in the absence of neurotrophin receptor ligands. Neuronal degeneration is assessed using morphological criteria 48 hours following cell seeding. The neurotrophins brain-derived neurotrophic factor (BDNF) and nerve growth factor (NGF) serve as positive controls. The maximum cell death preventing activity of BDNF is defined as 100% neurotrophic activity. The efficacy of NGF is 80% of that of BDNF. The neurotrophic activity of the test compounds at each applied concentration is quantitated in terms of a percentage of the maximum BDNF-supported survival level. In the presence of culture medium (CM) and the absence of BDNF or compounds, survival is approximately 40% of the BDNF maximum effect and this is regarded as baseline survival. For each compound, dose-response curves are generated and the $EC_{50}$ and maximum survival percentage are derived.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

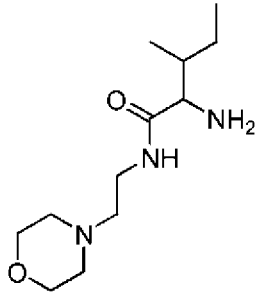

What is claimed is:

1. A compound of Formula I, II, IIIA, IIIB, or IV, wherein Formula I has the structure:

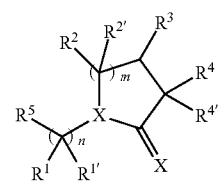

or a pharmaceutically acceptable salt, ester, prodrug or solvate thereof, wherein:
each of $R^1$, $R^{1'}$, $R^2$, $R^{2'}$, $R^3$, and $R^4$ is independently hydrogen, deuterium, optionally substituted alkyl, or optionally substituted deuterated-alkyl; or $R^2$ and $R^{2'}$ taken together form =O, =S, =CH$_2$, =CHD, or =CD$_2$;
$R^{4'}$ is hydrogen or deuterium;
$R^5$ is heterocycloalkyl or deuterated-heterocycloalkyl;
X is CH$_2$, CDH, CD$_2$, NH, O or S;
n is 0, 1, 2, 3, 4, or 5; and
m is 1 or 2;
with the proviso that the compound of Formula I comprises at least one carbon-bound deuterium with at least 45% deuterium incorporation;
wherein Formula II has the structure:

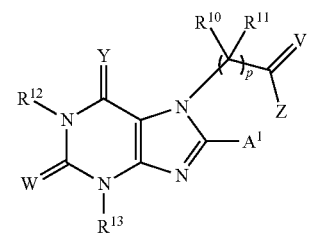

or a pharmaceutically acceptable salt, ester, prodrug or solvate thereof, wherein:
p is 0, 1, 2, 3, 4, 5, or 6;
$A^1$ is hydrogen or deuterium;
each of Y, V, and W is independently CH$_2$, CDH, CD$_2$, NH, O, or S;
each of $R^{10}$ and $R^{11}$ is independently hydrogen, deuterium, optionally substituted alkyl, or optionally substituted deuterated-alkyl;
each of $R^{12}$ and $R^{13}$ is independently hydrogen, —NR$^a$R$^b$, —OH, —C(=O)OR$^a$, —C(=O)NHR$^a$, —NHC(=O)R$^a$, —NHS(=O)$_2$R$^a$, optionally substituted alkyl, or optionally substituted deuterated-alkyl;
each of R$^a$ and R$^b$ is independently hydrogen, optionally substituted alkyl, or optionally substituted deuterated-alkyl; and
Z is an optionally substituted heterocycloalkyl, an optionally substituted deuterated-heterocycloalkyl, an optionally substituted heteroaryl, an optionally substituted deuterated-heteroaryl, or

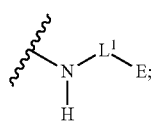

L¹ is a linking group selected from the group consisting of optionally substituted alkylene, optionally substituted deuterated-alkylene, optionally substituted cycloalkylene, optionally substituted deuterated-cycloalkylene, optionally substituted alkenylene, optionally substituted deuterated-alkenylene, optionally substituted arylene, optionally substituted deuterated-arylene, optionally substituted cycloalkenylene, and optionally substituted deuterated-cycloalkenylene;

E is selected from the group consisting of:

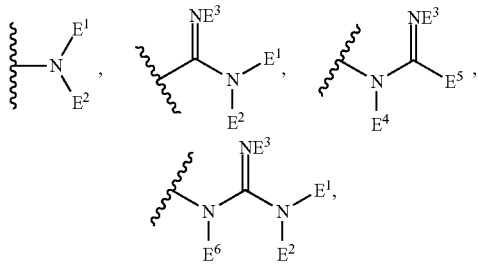

pyrrolidinyl, and deuterated-pyrrolidinyl;

each of E¹, E², E⁴, E⁵, and E⁶ independently is selected from the group consisting of hydrogen, optionally substituted alkyl, optionally substituted deuterated-alkyl, optionally substituted cycloalkyl, optionally substituted deuterated-cycloalkyl, optionally substituted aryl, optionally substituted deuterated-aryl, optionally substituted arylalkyl, and optionally substituted deuterated-arylalkyl;

each E³ is independently selected from the group consisting of hydrogen, hydroxyl, optionally substituted alkyl, optionally substituted deuterated-alkyl, optionally substituted aryl, optionally substituted deuterated-aryl, acyloxyl, alkoxyl, and deuterated-alkoxyl;

with the proviso that the compound of Formula II comprises at least one carbon-bound deuterium with at least 45% deuterium incorporation;

wherein Formula IIIA has the structure:

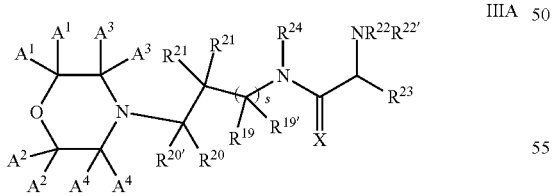

IIIA or a pharmaceutically acceptable salt, ester, prodrug or solvate thereof, wherein:

X is CH₂, CDH, CD₂, NH, O or S;

each of A¹, A², A³, and A⁴ is independently hydrogen or deuterium;

s is 0, 1, 2, 3 or 4;

each of $R^{19}$, $R^{19'}$, $R^{20}$, $R^{20'}$, $R^{21}$, $R^{21'}$, $R^{22}$, $R^{22'}$ and $R^{24}$ is independently hydrogen, deuterium, optionally substituted alkyl, or optionally substituted deuterated-alkyl; or $R^{20}$ and $R^{20'}$ taken together form =O, =S, =CH₂, =CDH, or =CD₂; or $R^{20}$ and $R^{21}$ taken together with the atoms to which they are attached form an optionally substituted cycloalkyl or optionally substituted deuterated-cycloalkyl; or $R^{20}$ and $R^{21}$ taken together with the atoms to which they are attached form an optionally substituted aryl or optionally substituted deuterated-aryl; or $R^{19}$ and $R^{20}$ taken together with the atoms to which they are attached form an optionally substituted cycloalkyl or optionally substituted deuterated-cycloalkyl; or $R^{19}$ and $R^{20}$ taken together with the atoms to which they are attached form an optionally substituted aryl or optionally substituted deuterated-aryl; and $R^{23}$ is optionally substituted alkyl, optionally substituted cycloalkyl or optionally substituted aryl or optionally substituted deuterated-aryl; or $R^{22}$ and $R^{23}$ taken together with the atoms to which they are attached form an optionally substituted heterocycloalkyl or optionally substituted deuterated-heterocycloalkyl;

with the proviso that the compound of Formula IIIA comprises at least one carbon-bound deuterium with at least 45% deuterium incorporation;

wherein Formula IIIB has the structure:

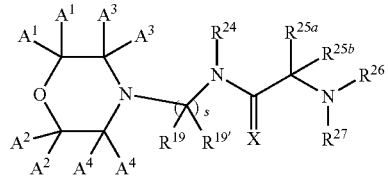

IIIB or a pharmaceutically acceptable salt, ester, prodrug or solvate thereof, wherein:

X is CH₂, CDH, CD₂, NH, O or S;

each of A¹, A², A³, A⁴, and $R^{25a}$ is independently hydrogen or deuterium;

s is an integer from 1 to 8;

each of $R^{19}$, $R^{19'}$, $R^{26}$, and $R^{27}$ is independently hydrogen, deuterium, optionally substituted alkyl, or optionally substituted deuterated-alkyl;

$R^{24}$ is hydrogen, optionally substituted alkyl, or optionally substituted deuterated-alkyl;

$R^{25b}$ is hydrogen, deuterium, halo, hydroxyl, alkoxy, deuterated-alkoxy, optionally substituted alkyl, optionally substituted deuterated-alkyl, optionally substituted cycloalkyl, optionally substituted deuterated-cycloalkyl, optionally substituted aryl, or optionally substituted deuterated-aryl;

with the proviso that the compound of Formula IIIB comprises at least one carbon-bound deuterium with at least 45% deuterium incorporation; and wherein Formula IV has the structure:

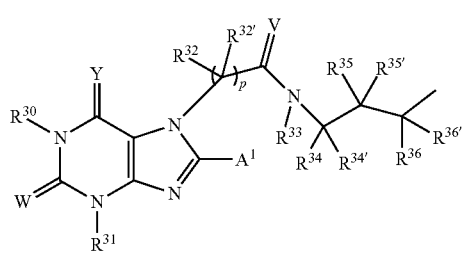

IV or a pharmaceutically acceptable salt, ester, prodrug or solvate thereof, wherein:

p is 1, 2, 3, 4, 5, or 6;

each of Y, V, and W is independently $CH_2$, CDH, $CD_2$, NH, O or S;

$A^1$ is hydrogen or deuterium;

each of $R^{30}$, $R^{31}$, $R^{32}$, $R^{32'}$, $R^{33}$, $R^{34}$, $R^{34'}$, $R^{35}$, $R^{35'}$, $R^{36}$, and $R^{36'}$ is independently hydrogen, deuterium, optionally substituted alkyl, or optionally substituted deuterium-alkyl; or $R^{34}$ and $R^{36}$ taken together with the atoms to which they are attached form an optionally substituted carbocyclic ring or optionally substituted deuterated-carbocyclic ring;

E is —$CHR^cR^d$, —$CDR^cR^d$, —$NR^cR^d$, —$OR^c$, or —$SR^C$; and each of $R^c$ and $R^d$ is independently hydrogen, deuterium, optionally substituted deuterated-alkyl, or optionally substituted alkyl; or $R^c$ and $R^d$ taken together with the nitrogen atom to which they are attached form an optionally substituted heterocyclic ring or optionally substituted deuterated-heterocyclic ring; or $R^c$ and $R^d$ taken together with the carbon atom to which they are attached form an optionally substituted carbocyclic ring or optionally substituted deuterated-carbocyclic ring;

with the proviso that the compound of Formula IV comprises at least one carbon-bound deuterium with at least 45% deuterium incorporation.

2. The compound of claim 1 having the structure of Formula II:

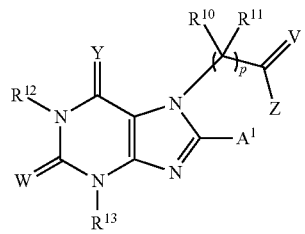

II or a pharmaceutically acceptable salt, ester, prodrug or solvate thereof.

3. The compound of claim 2 having the structure of Formula IIB:

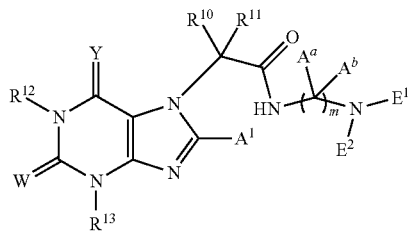

IIB or a pharmaceutically acceptable salt, ester, prodrug or solvate thereof.

4. The compound of claim 2, having the following structure in deuterated form:

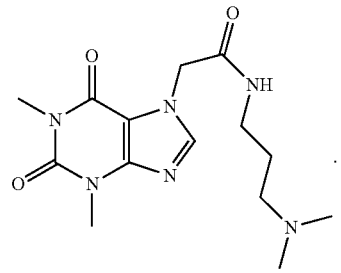

5. The compound of claim 1 having the structure of Formula IIIB

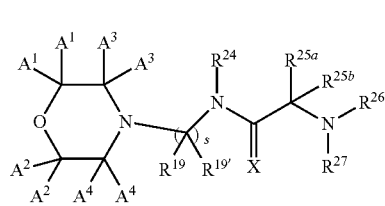

IIIB or a pharmaceutically acceptable salt, ester, prodrug or solvate thereof.

6. The compound of claim 5, wherein X is oxygen and $R^{24}$ is hydrogen.

7. The compound of claim 5 having the following structure in a deuterated form:

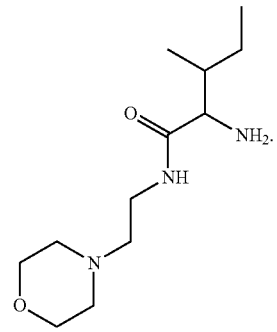

8. The compound of claim 5 selected from the group consisting of:

deuterated-(2S,3S)-2-amino-3-methyl-N-(2-morpholinoethyl)-pentanamide;

deuterated-(2R,3R)-2-amino-3-methyl-N-(2-morpholinoethyl)-pentanamide;

deuterated-(2R,3S)-2-amino-3-methyl-N-(2-morpholinoethyl)-pentanamide;

deuterated-(2S,3R)-2-amino-3-methyl-N-(2-morpholinoethyl)-pentanamide; and a mixture thereof;

or a pharmaceutically acceptable salt, solvate, ester, or prodrug thereof.

9. A pharmaceutical composition comprising a compound of claim 1, or a pharmaceutically acceptable salt, solvate, ester, or prodrug thereof; and a pharmaceutically acceptable carrier.

10. A method for treating a disorder involving degeneration or dysfunction of cells expressing p75 comprising administering to a patient in need of such treatment a pharmaceutical composition comprising a compound of claim 1 or a pharmaceutically acceptable salt, solvate, ester, or prodrug thereof.

11. The method of claim 10 wherein the disorder is a neurodegenerative disorder.

12. The method of claim 10 wherein the disorder is selected from the group consisting of Alzheimer's disease, Huntington's disease, Pick's disease, amyotrophic lateral sclerosis, epilepsy, Parkinson's disease, spinal cord injury, stroke, hypoxia, ischemia, brain injury, diabetic neuropathy, peripheral neuropathy, nerve transplantation, multiple sclerosis, peripheral nerve injury, retinal degeneration, and hair loss.

13. The method of claim 12 wherein the disorder is selected from the group consisting of Alzheimer's disease, Huntington's disease, epilepsy, spinal cord injury, ischemia, brain injury, peripheral neuropathy, retinal degeneration, and hair loss.

* * * * *

UNITED STATES PATENT AND TRADEMARK OFFICE
CERTIFICATE OF CORRECTION

PATENT NO. : 9,464,066 B2
APPLICATION NO. : 14/230833
DATED : October 11, 2016
INVENTOR(S) : Damodara Gopal Page 1 of 3

It is certified that error appears in the above-identified patent and that said Letters Patent is hereby corrected as shown below:

In the Claims

Claim 1, Column 54, Line 10 (Structure I), replace the following structure:

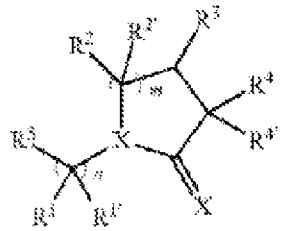

With the following structure:

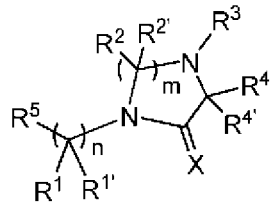

Claim 1, Column 55, Line 50 (Structure IIIA), replace the following structure:

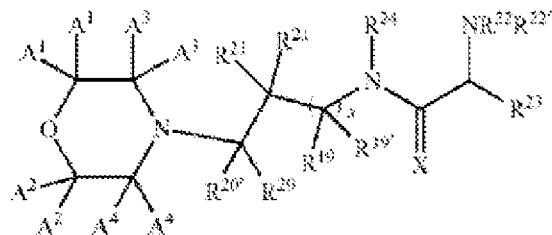

Signed and Sealed this
Fifth Day of September, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,464,066 B2

Page 2 of 3

With the following structure:

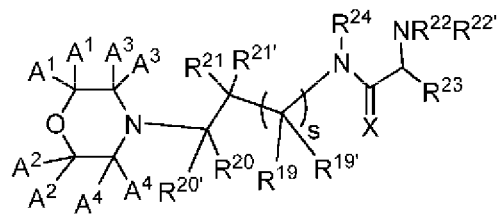

Claim 1, Column 56, Line 60 (Structure IV), replace the following structure:

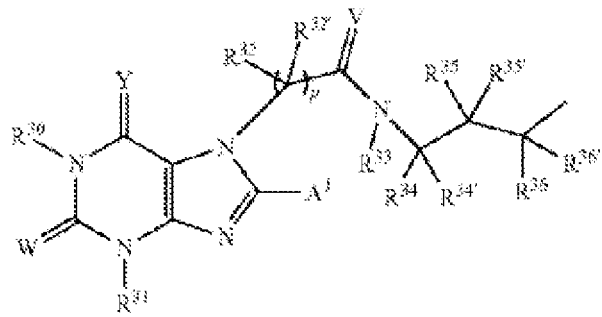

With the following structure:

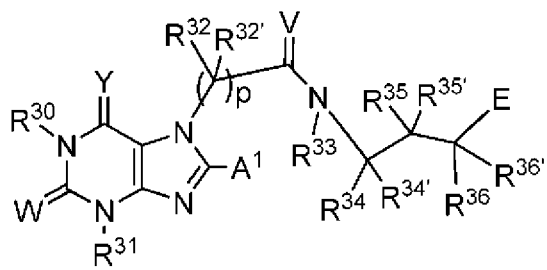

Claim 3, Column 57, Line 55 (Structure IIB), replace the following structure:

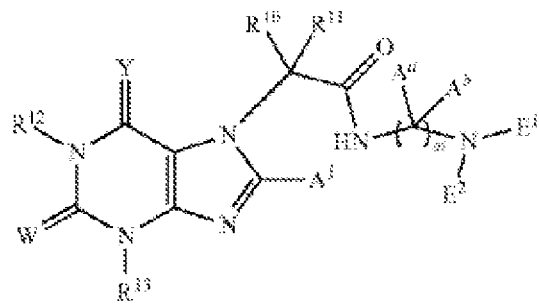

CERTIFICATE OF CORRECTION (continued)
U.S. Pat. No. 9,464,066 B2

With the following structure:

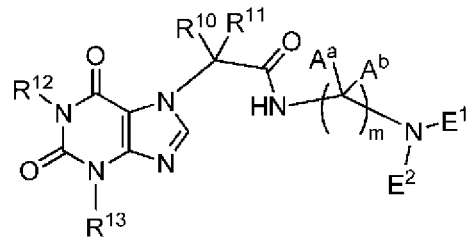

Claim 7, Column 58, Line 40, replace the following structure:

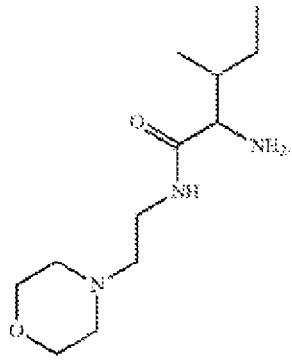 [SMILES: CCC(C)C(N)C(=O)NCCN1CCOCC1]

With the following structure: